United States Patent
Cuttitta et al.

(10) Patent No.: US 7,364,719 B2
(45) Date of Patent: Apr. 29, 2008

(54) VASOREGULATING COMPOUNDS AND METHODS OF THEIR USE

(75) Inventors: Frank Cuttitta, Adamstown, MD (US); Alfredo Martinez, Bethesda, MD (US); William G. Stetler-Stevenson, Kensington, MD (US); Edward J. Unsworth, Kensington, MD (US); Juan M. Saavedra, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 179 days.

(21) Appl. No.: 10/529,118

(22) PCT Filed: Oct. 3, 2003

(86) PCT No.: PCT/US03/31400

§ 371 (c)(1),
(2), (4) Date: Mar. 24, 2005

(87) PCT Pub. No.: WO2004/032708

PCT Pub. Date: Apr. 22, 2004

(65) Prior Publication Data

US 2005/0261179 A1    Nov. 24, 2005

Related U.S. Application Data

(60) Provisional application No. 60/416,291, filed on Oct. 4, 2002.

(51) Int. Cl.
A61K 49/00 (2006.01)

(52) U.S. Cl. ............... 424/9.1; 424/1.11; 424/1.65; 424/1.69; 424/9.2

(58) Field of Classification Search ............ 424/1.11, 424/1.65, 1.69, 9.1, 9.2; 530/300, 327; 206/223, 206/569, 570
See application file for complete search history.

(56) References Cited

U.S. PATENT DOCUMENTS

| | | | |
|---|---|---|---|
| 5,175,343 A * | 12/1992 | Fritzberg et al. ............ 560/145 |
| 5,639,855 A | 6/1997 | Kitamura et al. |
| 5,830,703 A | 11/1998 | Kitamura et al. |
| 5,831,004 A | 11/1998 | Campbell et al. |
| 5,837,823 A | 11/1998 | Kitamura et al. |
| 5,910,416 A | 6/1999 | Kitamura et al. |
| 6,117,869 A | 9/2000 | Picard et al. |
| 6,133,304 A | 10/2000 | Peterson, Jr. et al. |
| 6,265,432 B1 | 7/2001 | Purchase, Jr. et al. |
| 6,307,101 B1 | 10/2001 | Campbell et al. |
| 6,320,022 B1 | 11/2001 | Cuttitta et al. |
| 6,339,160 B1 | 1/2002 | Politi et al. |
| 6,350,885 B1 | 2/2002 | O'Brien et al. |
| 6,440,421 B1 | 8/2002 | Cornish et al. |
| 2002/0055615 A1 | 5/2002 | Cutitta et al. |

FOREIGN PATENT DOCUMENTS

| | | |
|---|---|---|
| EP | 0 845 036 | 6/1999 |
| EP | 0 926 238 A2 | 11/2000 |
| EP | 0 926 238 A3 | 11/2000 |
| WO | WO 97/07214 | 2/1997 |
| WO | WO 01/18550 | 3/2001 |
| WO | WO 2004/043383 | 5/2004 |

OTHER PUBLICATIONS

Corti et al., "Vasopeptidase Inhibitors: A New Therapeutic Concept in Cardiovascular Disease," *Cardiovascular Drugs* 104:1856-1862 (Oct. 9, 2001).
Fernandez-Patron, "Vascular Matrix Metalloproteinase-2-Dependent Cleavage of Calcionin Gene-Related Peptide Promotes Vasoconstriction," *Circ Res.* 87:670-676 (2000).
Kitamura et al., "Cloning and characterization of cDNA encoding a precursor for human adrenomedullin," *Biochem. Biophys. Res. Comm.* 194:720-725 (1993).
Kitamura et al., "Adrenomedullin (11-26): a novel endogenous hypertensive peptide isolated from bovine adrenal medulla," *Peptides* 22:1713-1718 (2001).
Lewis et al., "Degradation of human adrenomedullin (1-52) by plasma membrane enzymes and identification of metabolites," *Peptides* 18(5):733-739 (1997).
Watanabe et al., "Vasopressor activity of N-terminal fragments of adrenomedullin in anesthetized rat," *Biochem. Biophys. Res. Comm.* 219:59-63 (1996).
Belloni et al., "Proadrenomedullin N-Terminal 20 Peptide (PAMP), Acting Through PAMP(12-20)-Sensitive Receptors, Inhibits $Ca^{2+}$-Dependent, Agonist-Stimulated Secretion of Human Adrenal Glands," *Hypertension* 33:1185-1189 (1999).
Calvo et al., "Adrenomedullin and proadrenomedullin N-terminal 20 peptide in the normal prostate and in prostate carcinoma," *Microsc. Res. Tech.* 57(2):98-104 (Apr. 2002) *Abstract Only*.
Champion et al., "Proadrenomedullin NH2-terminal 20 peptide has direct vasodilator activity in the cat," *Am. J. Physiol.* 272(4 Pt 2):R1047-54 (Apr. 1997) *Abstract Only*.
Champion et al., "Tone-dependent vasodilator responses to proadrenomedullin NH2-terminal 20 peptide in the hindquarters vascular bed of the rat," *Peptides* 18(4):513-519 (1997) *Abstract Only*.

(Continued)

*Primary Examiner*—Dameron L. Jones
(74) *Attorney, Agent, or Firm*—Klarquist Sparkman, LLP; Gillian L. Bunker

(57) ABSTRACT

Methods and compounds are described for regulating blood pressure in a subject. Specific embodiments are methods for reversing vasodilation of blood vessels, by administering to a subject a therapeutically effective amount peptide AM(11-22). The vasoconstrictor can be used for a variety of purposes, including hemostasis or the treatment of shock, for example vasodilatory shock syndromes such as septic shock. Other specific embodiments are methods for reversing vasoconstriction of blood vessels, by administering to a subject a therapeutically effect amount of an inhibitor of AM(11-22), sufficient to reduce hypertension in the subject. Compounds and pharmaceutical compositions are also provided, as are kits.

22 Claims, 5 Drawing Sheets

OTHER PUBLICATIONS

Eto et al., "Adrenomedullin and proadrenomedullin N-terminal 20 peptide: vasodilatory peptides with multiple cardiovascular and endocrine actions," *Trends in Endo and Metab.* 12(3):91-93 (Apr. 1, 2001) *Abstract Only.*

Fry et al., "Proadrenomedullin NH2-terminal peptide (PAMP) (12-20) has vesodepressor activity in the rat and cat," *Life Science* 60(10):PL161-167 (1997) *Abstract Only.*

Ishimitsu et al., "Genomic structure of human adrenomedullin gene," *Biochem Biophys Res Commun* 203(1):631-639 (Aug. 30, 1994) *Abstract Only.*

Kanagawa et al., "Adrenomedullin: a new hypotensive peptide," *J. Hypertens Suppl.* 14(5):S105-110 (Dec. 1996) *Abstract Only.*

Kapas et al., "Regulation of PAMP and adrenomedullin receptor expression in the rat adrenal zona glomerulosa" *Endoc Res.* 24(3-4):717-20 (Aug.-Nov. 1998) *Abstract Only.*

Kitamura et al., "Identification and hypotensive activity of proadrenomedullin N-terminal 20 peptide (PAMP)," *FEBS Letters* 351(1):35-7 (Aug. 29, 1994) *Abstract Only.*

Kuwasako et al., "Increased plasma proadrenomedullin N-terminal 20 peptide in patients with essential hypertension," *Ann Clin Biochem.* 36:(pt5):622-628 (Sep. 1999) *Abstract Only.*

Lisy et al., "Neutral endopeptidase inhibition potentiates the natriuretic actions of adrenomedullin," *Am. J. Physiol.* 275:F410-F414 (1998).

Makino et al., "Attenuated hypotensive response to proadrenomedullin N-terminal 20 peptide in pregnant rats: modulation by steroid hormones," *Peptides* 20(12):1521-1525 (1999) *Abstract Only.*

Martínez et al., "Proadrenomedullin $NH_2$-Terminal 20 Peptide is a Potent Angiogenic Factor, and its Inhibition Results in Reduction of Tumor Growth," *Cancer Res* 64:6489-6496 (Sep. 15, 2004).

Martínez et al., "The Effects of Adrenomedullin Overexperssion in Breast Tumor Cells," *J. Nat. Cancer Inst.* 94(16):12 pages (Aug. 21, 2002).

Matsui et al., "Biosynthesis and Secretion of Adrenomedullin and Proadrenomedullin N-Terminal 20 Peptide in a Rat Model of Endotoxin Shock," *Hypertens* 24:543-549 (2001).

Matsui et al., "Lack of hypotensive effect of chronically infused proadrenomedullin N-terminal 20 peptide in rats," *Horm Metab Res* 30(9):555-6 (1998) *Abstract Only.*

Moody et al., "Adrenomedullin binds with high affinity, elevates cyclic AMP, and stimulates c-fos mRNA in C6 glioma cells," *Peptides* 18(8):1111-1115 (1997) *Abstract Only.*

Nakamura et al., "Comparison of vasodilator potency of adrenomedullin and proadrenomedullin N-terminal 20 peptide in human," *Life Sci.* 65(20):2151-2156 (1999) *Abstract Only.*

Nossaman et al., "Effects of Phentolamine on Responses to PAMP in the Hindquarters Vascular Bed of the Rat," *J. Cardiovasc. Pharmacol Ther.* 2(3):153-157 (Jul. 1997) *Abstract Only.*

Robert et al., "Differential regulation of matrix metalloproteinases associated with aging and hypertension in the rat heart," *Lab Invest.* 76(5):729-738 (May 1997) *Abstract Only.*

Saita et al., "Cardiovascular and sympathetic effects of proadrenomedullin NH2-terminal 20 peptide in conscious rats," *Regul Pept* 77(1-3):147-153 (Oct. 16, 1998) *Abstract Only.*

Samson et al., "Central mechanisms for the hypertensive effects of preproadrenomedullin-derived peptides in conscious rats," *Am J. Physiol* 274:R1505-R1509 (1998).

Samson, "Proadrenomedullin-derived peptides," *Front Neuroendocrinol.* 19(2):100-27 (Apr. 1998) *Abstract Only.*

Shimosawa et al., "A Newly Identified Peptide, Proadrenomedullin N-Terminal 20 Peptide, Induces Hypotensive Action via Pertussis Toxin-Sensitive Mechanisms," *Hypertension* 30:1009-1014 (1997).

Shimosawa et al., "Adrenomedullin, an Endogenous Peptide, Counteracts Cardiovascular Damage," *Circulation* 105:106-111 (2002).

Shimosawa and Fujito, "Hypotensive Effect of a Newly Identified Peptide, Proadrenomedullin N-Terminal 20 Peptide," *Hypertension* 28:325-329 (1996).

Uemura et al., "Aldosterone augments adrenomedullin production without stimulating pro-adrenomedullin N-terminal 20 peptide secretion in vascular smooth muscle cells," *J. Hypertens.* 20(6):1209-1214 (Jun. 2002) *Abstract Only.*

Wilkinson et al., "Adrenomedullin (ADM) in the human forearm vascular bed: effect of neutral endopeptidase inhibition and comparison with proadrenomedullin $NH_2$-terminal 20 peptide (PAMP)," *J. Clin Pharm* 52:159-164 (2001).

Zhao et al., "PCR display identifies tamoxifen induction of the novel angiogenic factor adrenomedullin by a non estrogenic mechanism in the human endometrium," *Oncogene* 16(3):409-415 (Jan. 22, 1998) *Abstract Only.*

Corcoran et al., "MMP-2: Expression, Activation and Inhibition," *Enzyme Protein* 49:7-19 (1996).

Giannelli and Antonaci, "Gelantinases and their inhibitors in tumor metastasis: form biological research to medical applications," *Histol Histopathol* 17:339-345 (2002).

Kleiner and Stetler-Stevenson, "Matrix metalloproteinases and metastasis," *Cancer Chemother Pharmacol* 43(Suppl):S42-S51 (1999).

Kugler et al., "Matrix Metalloproteinases and their Inhibitors," *Anticancer Research* 19:1589-1592 (1999).

Goffin et al., "Human Endometrial Epithelial Cells Modulate the Activation of Gelatinase A by Stromal Cells," *Gynecol Obstet Invest* 53:105-111 (2002).

Martinez et al., "Matrix metalloproteinase-2 cleavage of adrenomedullin produces a vasoconstrictor out of a vasodilator" *Biochem. J.* (2004) 383, 413-418.

Supplementary Partial European Search Report (dated Oct. 30, 2007), European Application No. 03774543.7.

\* cited by examiner

VASOREGULATING COMPOUNDS AND METHODS OF THEIR USE

CROSS REFERENCE TO RELATED APPLICATIONS

This is a § 371 U.S. national stage of PCT/US2003/031400, filed Oct. 3, 2003, which was published in English under PCT Article 2(2), and claims the benefit of U.S. Provisional Application No. 60/416,291, filed Oct. 4, 2002. Both applications are incorporated herein in their entirety.

FIELD OF THE DISCLOSURE

The present disclosure concerns peptides and compositions, such as pharmaceutical compositions, that are useful as vasoregulating compounds, and the use of these, for example to influence blood pressure. Particular embodiment compounds are particularly useful for reducing blood pressure, while others are particularly useful for increasing blood pressure.

BACKGROUND OF THE DISCLOSURE

Methods for influencing blood pressure, both to lower and to raise it, are extremely important because many serious diseases and conditions involve aberrations in blood pressure.

Hypertension is a major public health problem due to its high prevalence and increased risk of cardiovascular morbidity and mortality (Yildirir et al. *Europace* 4:175-182, 2002; Mulvany, *News Physiol. Sci.* 17:105-109, 2002). Systemic hypertension is the most prevalent cardiovascular disorder in the United States, affecting over 60 million Americans. In spite of increasing public awareness and a rapidly expanding array of antihypertensive medications, hypertension remains one of the leading causes of cardiovascular morbidity and mortality. Hypertension treatments have focused on stimulating the relaxation of the peripheral vasculature (vasodilation), depressing cardiac function, or by stimulating salt transport by blocking epithelial transport of sodium or chloride (diuresis) ("Textbook of Medical Physiology", Guyton and Hall, eds. p. 234, 1996, W. B. Saunders). In addition, adverse metabolic effects have been observed with treatment using certain classes of antihypertensive treatment in coronary disease prevention ("Cecil Textbook of Medicine" pp. 252-269 (1992) W. B. Saunders).

At the other end of the spectrum, shock is a condition in which blood perfusion of peripheral tissues is inadequate to sustain normal tissue metabolism. The fundamental defect in this condition is usually hypotension, so that oxygen delivery or uptake is inadequate for aerobic metabolism. This defect results in a shift to anaerobic metabolism, with increased production and accumulation of lactic acid. When shock persists, impaired organ function is followed by irreversible cell damage and death.

The major causes of shock are hypovolemic shock (often from acute hemorrhage), cardiogenic shock (for example from arrhythmia or heart failure), and vasodilatory shock (caused by vascular dilation, as seen for example in cerebral trauma, drug intoxication, heat exposure, or septic shock accompanying a gram negative bacterial infection). The symptoms and signs of shock are well known to the clinician, and include lethargy, confusion, cold extremities that are often moist and cyanotic, prolonged capillary filling time, a weak and rapid pulse, and (ultimately) profound hypotension.

Septic shock is a type of vasodilatory shock that is often accompanied by a clinical presentation that suggests infection, such as fever, chills, warm, flushed skin, and hemodynamic instability (characterized by a falling and rising blood pressure). Septic shock is an often fatal condition that accompanies severe microbial infections, frequently with gram-negative bacteria such as *Escherichia coli, Pseudomonas aeruginosa* and *Klebsiella* or *Bacteroides* species. Gram-positive bacterial infections can also lead to septic shock, particularly those infections caused by *Staphylococcus aureus* and the *Pneumococcus*. The bacterial infections can be acquired by routes such as ingestion, personal contact, or trauma, but infections are often nosocomial consequences of therapeutic procedures, including implantation of indwelling catheters or prosthetic devices. Septic shock often occurs in immunocompromised subjects, and therefore has been an increasing problem in recent years because of the increasing number of individuals who are immunocompromised. For example, subjects with HIV disease or who are taking immunosuppressive drugs for the treatment of cancer or organ transplantation rejection are at increased risk of developing septic shock.

In view of the above, there exists a need for agents that counteract aberrations in blood pressure, including hypotension and the vasodilation associated with shock.

SUMMARY OF THE DISCLOSURE

This disclosure provides compounds that are useful as vasoconstrictors or vasodilators, and methods of their use.

Provided herein in one embodiment is a vasoconstrictor molecule that is a peptide derived from adrenomedullin (AM) (SEQ ID NO: 3); the peptide comprises amino acids 11-22 of AM, and is referred to herein as AM(11-22) (SEQ ID NO: 4). Methods of using this peptide are also provided, for instance for treating hypotensive condition, such as shock.

The AM(11-22) compound can be used in any clinical or laboratory situation in which reversal of vasodilation is desired, for example in laboratory preparations (such as drug screening assays), or for inducing therapeutic (including diagnostic) vasoconstriction. There is a wide spectrum of therapeutic uses, such as inducing vasoconstriction (and therefore inhibiting blood flow) following traumatic or surgical injury. The method can also be applied to treat shock or other hemodynamic instabilities, for example vasodilatory shock conditions, such as septic shock or hemorrhagic shock.

In yet other embodiments, AM(11-22) may be incorporated into a pharmaceutical composition that includes a therapeutically effective amount of the compound and a pharmaceutical carrier.

Still other embodiments are methods of screening for an inhibitor of AM(11-22). The methods include determining whether a compound inhibits AM(11-22)-mediated vasoconstriction; inhibition of AM(11-22)-mediated vasoconstriction indicates that the compound is an AM(11-22) inhibitor.

The foregoing and other features and advantages will become more apparent from the following detailed description of several embodiments, which proceeds with reference to the accompanying figures.

BRIEF DESCRIPTION OF THE FIGURES

FIG. 5A is a graph showing that intact AM and the two larger fragments induced a significant elevation of cAMP when compared to addition of phosphate buffered saline (PBS) (control), whereas the rest of the test peptides did not have any effect on the levels of cAMP; *: P<0.001. FIG. 5B is a graph showing that addition of different concentrations of AM(11-22) did not affect the response elicited by the intact peptide, AM (1-52). The control value is significantly different from all the treatments (*: P<0.001) but these are statistically indistinguishable among themselves. Bars represent the mean ± standard deviation of 8 independent measurements.

SEQUENCE LISTING

Figure 1:
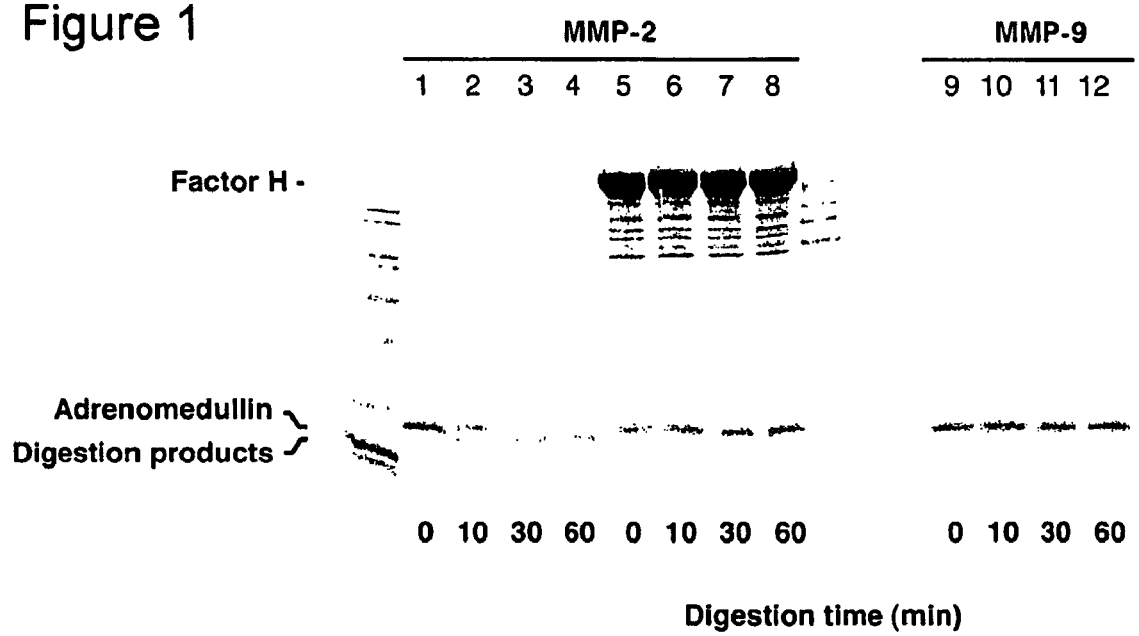
FIG. 1 is an image of protein gels, showing that matrix metalloproteinase (MMP)-2 but not MMP-9 degrades AM in the absence of complement factor H. Synthetic AM was exposed to MMP-2 (lanes 1-8) or MMP-9 (lanes 9-12) in the presence (lanes 5-8) or absence of factor H. Individual reactions were stopped with ethylenediaminetetraacetic acid (EDTA) at the indicated times and the resulting peptides separated by electrophoresis in 16% polyacrylamide gels. Lanes 1-4 show a progressive degradation of the original peptide and a concomitant appearance of digestion products.
Figure 2:
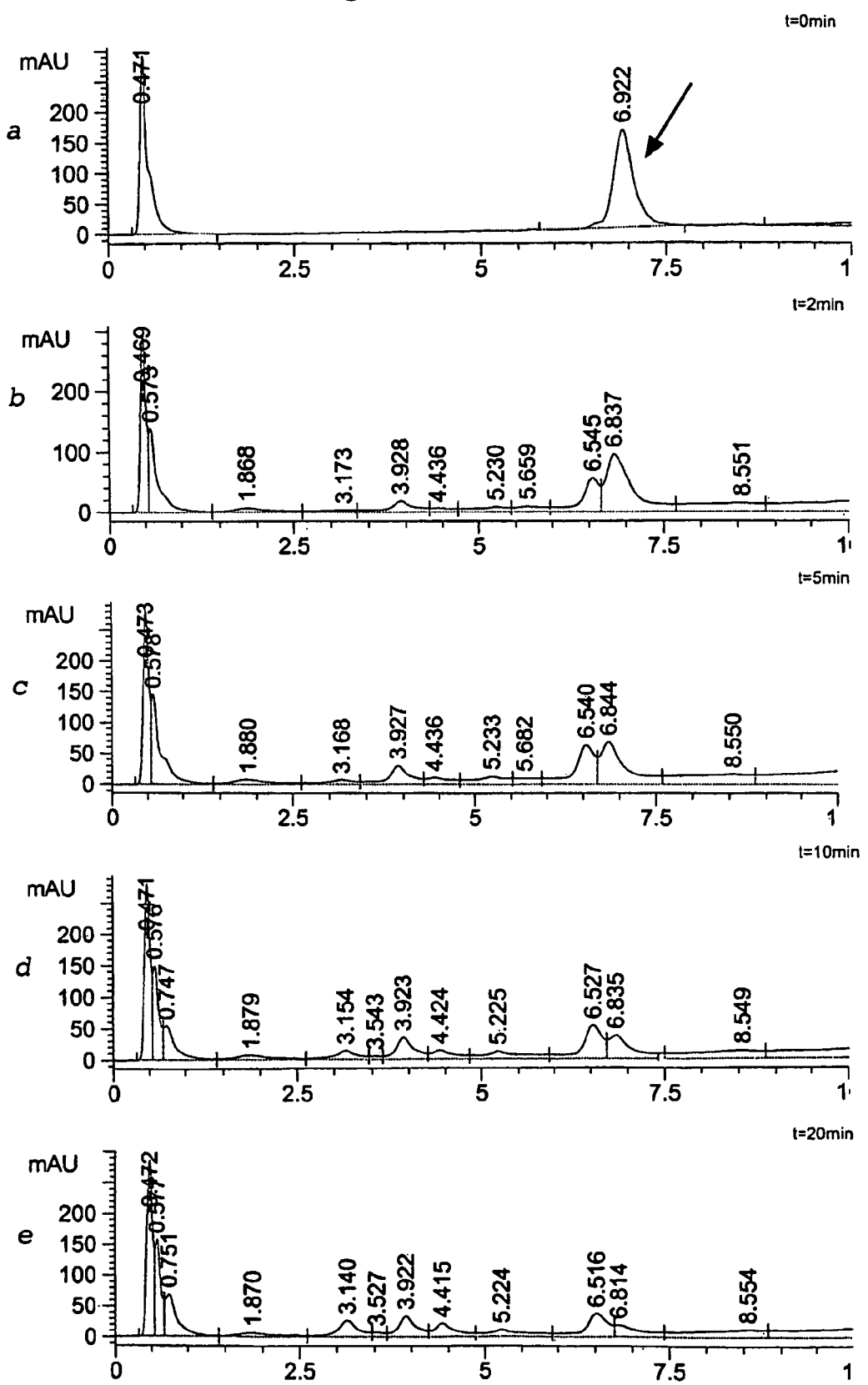
FIG. 2 is a series of high performance liquid chromatography (HPLC) charts, showing that MMP-2 digestion of AM generates novel peptide fragments. Digestion reactions were stopped at the indicated times and then analyzed by HPLC in a reverse phase column. The single peak at time=0 (arrow in a) corresponds to the intact AM peptide. This peak progressively diminished over time whereas additional peaks began to appear. The fractions exhibiting new peaks were analyzed by mass spectrometry.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The following sequences are included in this disclosure:

SEQ ID NO: 1 shows the nucleic acid sequence of preproadrenomedullin mRNA (available also as NM_001124), and the amino acid sequence of the protein encoded thereby.

SEQ ID NO: 2 shows the amino acid sequence of preproadrenomedullin (available also as NP_001115).

SEQ ID NO: 3 shows the amino acid sequence of adrenomedullin (2020431A), which corresponds to amino acid positions 65-146 of preproadrenomedullin (SEQ ID NO: 2).

SEQ ID NO: 4 shows the amino acid sequence of the peptide AM(11-22), which corresponds to positions 11-22 of adrenomedullin (SEQ ID NO: 3) and positions 105-116 of preproadrenomedullin (SEQ ID NO: 2).

DETAILED DESCRIPTION

I. Abbreviations

| | |
|---|---|
| A | adenine |
| AM | adrenomedullin |
| AM(11-22) | peptide consisting of amino acids 11-22 of adrenomedullin |
| C | cytosine |
| cAMP | cyclic adenosine monophosphate |
| cDNA | complementary deoxyribonucleic acid |
| CGRP | calcitonin gene-related peptide |
| CRLR | calcitonin-receptor-like |
| DNA | deoxyribonucleic acid |
| EDTA | ethylenediaminetetraacetic acid |
| G | guanine |
| HPLC | high performance liquid chromatography |
| IP | intraperitoneal |
| IV | intravenous |
| mRNA | messenger ribonucleic acid |
| PBS | phosphate buffered saline |
| PNA | peptide nucleic acid |
| RAMP | receptor activity modifying protein |
| RNA | ribonucleic acid |
| T | thymine |
| UTR | untranslated region |

II. Terms

Unless otherwise noted, technical terms are used according to conventional usage. Definitions of common terms in molecular biology may be found in Benjamin Lewin, *Genes*

V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Animal: Living multi-cellular vertebrate organisms, a category that includes, for example, mammals and birds. The term mammal includes both human and non-human mammals.

Antibody: The term "antibody" refers to a protein (or protein complex) that includes of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term antibodies includes intact immunoglobulins as well as a number of well-characterized fragments produced by digestion with various peptidases, or genetically engineered "artificial" antibodies. Thus, for example, pepsin digests an antibody below the disulfide linkages in the hinge region to produce F(ab)'$_2$, a dimer of Fab which itself is a light chain joined to $V_H$—$C_H$ 1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine (A), guanine (G), cytosine (C), and thymine (T) bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Injectable composition: A pharmaceutically acceptable fluid composition comprising at least one active ingredient, for example, a peptide derived from AM, such as AM(11-22). The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the compositions of this disclosure are conventional; appropriate formulations are well known in the art.

Isolated: An "isolated" biological component (such as a nucleic acid molecule, protein or organelle) has been substantially separated or purified away from other biological components in the cell of the organism in which the component naturally occurs, for example, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 500 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 300 nucleotides in length, for example a sequence (such as DNA or RNA) that is at least 6 bases, for example at least 8, 10, 15, 20, 25, 30, 35, 40, 45, 50, 100 or even 200 or more bases long, or from about 6 to about 50 bases, for example about 10-25 bases, such as 12, 15, 20, or 25 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Parenteral: Administered outside of the intestine, For example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide: "Peptides," "polypeptides," and "oligopeptides" are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (for example, the amino terminal) has a free amino group, while the terminal amino acid at the other end of the chain (for example, the carboxy terminal) has a free carboxyl group. As such, the term "amino terminus" (abbreviated N-terminus) refers to the free alpha-amino group on the amino acid at the amino terminal end of the peptide, or to the alpha-amino group (imino group when participating in a peptide bond) of an amino acid at any other location within the peptide. The term "carboxy terminus" (abbreviated C-terminus) refers to the free carboxyl group on the amino acid at the carboxy terminal end of a peptide, or to the carboxyl group of an amino acid at any other location within the peptide.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "pharmaceutical agent" or "drug" refers to a chemical compound or other composition (including peptide based pharmaceuticals) capable of inducing a desired therapeutic or prophylactic effect when properly administered to a subject.

Purified: The term purified does not require absolute purity; rather, it is intended as a relative term. Thus, for example, a purified peptide preparation is one in which the peptide is more enriched than it is in its generative environment, for instance within a cell or in a biochemical reaction chamber. Preferably, a preparation of peptide is purified such that the peptide represents at least 50% of the total protein content of the preparation.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

Similarly, a recombinant protein is one encoded for by a recombinant nucleic acid molecule.

Small molecule inhibitor: An inhibitor of at least one function of a target molecule, with a molecular weight preferably below about 1000 Daltons.

Subject: Living multi-cellular organisms, including vertebrate organisms, a category that includes both human and non-human mammals.

Therapeutic: A generic term that includes both diagnosis and treatment. Hence, therapeutic uses of a vasoconstrictor include diagnostic tests (such as vasoconstriction in a myocardial stress test) as well as administration for the inhibition, reversal or prevention of pathological conditions.

Therapeutically effective amount of [a vasoconstrictor or a vasodilator]: A quantity of compound, such as the peptide AM(11-22) or a specific inhibitor of MMP-2, sufficient to achieve a desired effect in a subject being treated. For instance, this can be the amount necessary to treat or ameliorate shock, or to measurably increase blood pressure over a period of time, or to measurably inhibit a decrease in blood pressure, in a subject. In some embodiments, it is the amount necessary to reduce blood pressure in a subject by a measurable amount over a period of time, or to measurably inhibit an increase in blood pressure, in a subject.

An effective amount of a vasoconstrictor may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can vary from about 0.001 mg/kg body weight to about 1 g/kg body weight. Alternatively, therapeutically effective amounts can be calculated in moles, for instance from about 0.5 nmol/kg to about 100 nmol/kg or more of an active ingredient.

The compounds discussed herein have equal application in medical and veterinary settings. Therefore, the general term "subject being treated" is understood to include all animals (for example, humans, apes, laboratory animals, companion animals, etc.) that are or may be suffering from an aberration in blood pressure, such as hypertension or hypotension.

Vasoconstriction. The diminution of the caliber or cross-sectional area of a blood vessel, for instance constriction of arterioles leading to decreased blood flow to a body part. This can be caused by a specific vasoconstrictor, an agent (for instance a chemical or biochemical compound) that causes, directly or indirectly, constriction of blood vessels. Such an agent can also be referred to as a vasohypertonic agent, and is said to have vasoconstrictive activity. A representative category of vasoconstrictors is the vasopressor (from the term pressor, tending to increase blood pressure), which term is generally used to refer to an agent that stimulates contraction of the muscular tissue of the capillaries and arteries.

Vasoconstriction also can be due to vasospasm, inadequate vasodilatation, thickening of the vessel wall, or the accumulation of flow-restricting materials on the internal wall surfaces or within the wall itself. Vasoconstriction is a major presumptive or proven factor in aging and in various clinical conditions including progressive generalized atherogenesis, myocardial infarction, stroke, hypertension, glaucoma, macular degeneration, migraine, hypertension and diabetes mellitus among others.

Vasodilation. A state of increased caliber of the blood vessels, or the act of dilation of a blood vessel, for instance dilation of arterioles leading to increased blood flow to a body part. This can be caused by a specific vasodilator, an agent (for instance, a chemical or biochemical compound) that causes, directly or indirectly, dilation of blood vessels. Such an agent can also be referred to as a vasohypotonic agent, and is said to have vasodilative activity.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

A first embodiment is a method of vasoconstricting blood vessels, which method involves administering to a subject a therapeutically effective amount of peptide AM(11-22) sufficient to induce vasoconstriction. In some examples of such method, the subject is experiencing or at risk of experiencing shock, for instance vasodilatory or septic shock.

Another embodiment is a pharmaceutical composition comprising a therapeutically effective amount of peptide AM(11-22), for instance an amount sufficient to induce a measurable increase in the blood pressure of a subject.

Yet another embodiment is peptide AM(11-22), for use in a pharmaceutical composition for inducing vasoconstriction, or for use in treating septic shock.

Also provided herein are kits for vasoconstricting blood vessels in a subject which kits include at least a container and an amount of peptide AM(11-22). In specific examples, the kit further includes a container comprising another vasoconstrictive, inotropic (for example, norepinephrine, dopamine, or dobutamine), or antibiotic agent. Optionally, any of these kits may further include instructions for administering the compound to a subject.

In certain embodiments, the method includes administering the compound to a subject experiencing or at risk for experiencing shock, and in particular examples, the shock is vasodilatory or septic shock. In certain examples, the method is a method of vasoconstricting blood vessels that are dilated.

In yet other embodiments, any of the foregoing compounds may be incorporated into a pharmaceutical composition that includes a therapeutically effective amount of the compound and a pharmaceutical carrier.

In still other embodiments, any of the foregoing compounds is incorporated into a kit. Optionally, the kit may include one or more other vasoconstrictive or inotropic, or antibiotic drugs. In particular examples, the vasoconstrictive or inotropic drug is norepinephrine, dopamine, or dobutamine.

Further embodiments are methods of screening for an inhibitor of AM(11-22). In such an embodiment, the method includes determining whether a compound inhibits AM(11-22)-mediated vasoconstriction. Inhibition of AM(11-22)-mediated vasoconstriction indicates that the compound is an AM(11-22) inhibitor. In particular examples of the method, determining whether a compound inhibits AM(11-22)-mediated vasoconstriction includes contacting a blood vessel with AM(11-22) in the presence and absence of the compound. In certain specific examples, the blood vessel is in a subject, and in even more particular examples, the subject is a rat. The compound can be any type of compound capable of inhibiting AM(11-22)-mediated vasoconstriction, for example, an antibody, for instance a monoclonal antibody, a small molecule inhibitor, or a peptide.

IV. Adrenomedullin and Related Peptides

Blood pressure is regulated by a complex interaction of vasoactive peptides and the sympathetic nervous system. One of these peptides, adrenomedullin (AM), is a potent and long-lasting endogenous vasodilator. Adrenomedullin, which is found in human pheochromocytoma, consists of 52 amino acids, has one intramolecular disulfide bond forming a ring structure of six residues, and shows slight homology with the calcitonin gene-related peptide (CGRP). Its carboxyl (C)-terminus tyrosine residue is amidated. AM has been proposed to function as a hormone in circulation control because it is found in blood in a considerable concentration. The activities of AM are mediated through a complex receptor system that includes the seven-transmembrane domain polypeptide calcitonin-receptor-like receptor (CRLR) and a single transmembrane domain protein, receptor activity modifying protein (RAMP) 2 or 3. Receptor activation with nanomolar concentrations of full length AM results in intracellular elevation of cAMP levels.

Adrenomedullin (AM) (SEQ ID NO: 3), a potent and long lasting vasodilator (López and Martínez, *Int. Rev. Cytol.* 221:1-92, 2002), is becoming increasingly attractive as a potential key mediator of blood pressure homeostasis. In addition, plasma AM levels are increased in cardiovascular diseases such as heart failure, hypertension, and septic shock, where AM seems to play a protective role (Eto, *Peptides* 22:1693-1711, 2001). AM is a 52 amino acid peptide with an internal disulfide bond between amino acids 16 and 21 and with an amidated tyrosine at the carboxy end (López and Martínez, *Int. Rev. Cytol.* 221:1-92, 2002). We have recently described the existence of a serum binding protein for AM and characterized it as complement factor H (Pío et al., *J. Biol. Chem.* 276:12292-12300, 2001). This binding interaction with factor H is able to increase the activity of AM in several experimental models but so far the molecular mechanism responsible for this enhancing effect is unknown (Pío et al., *J. Biol. Chem.* 276:12292-12300, 2001). The functions of AM are mediated through a complex receptor system that requires the presence of a seven-transmembrane domain polypeptide known as calcitonin-receptor-like receptor (CRLR) and the single-transmembrane domain protein, receptor activity modifying protein (RAMP) 2 or 3. Receptor activation with nanomolar concentrations of AM results in intracellular elevation of cAMP levels (McLatchie et al., *Nature* 393:333-339, 1998).

A number of smaller peptide fragments, some of which are vasoactive, are produced when AM is enzymatically digested. For example, Lewis et al. (*Peptides,* 18(5):733-739, 1997) identified a number of metabolites produced when human AM is degraded by plasma membrane enzymes. These include AM(2-52), AM(8-52), AM(26-52), AM(27-52), AM(28-52), and AM(33-52). In addition, Watanabe et al. (*Biochem. Biophys. Res. Comm.,* 219:59-63, 1996) synthesized several synthetic N-terminal AM fragments, including AM-(1-25)-$NH_2$, AM-(1-31)-$NH_2$, AM-(1-25)-OH, AM-(1-21)-$NH_2$, acetyl-AM-(16-21)-$NH_2$, and acetyl-AM-(16-36)-$NH_2$. Of these, AM-(1-25)-$NH_2$ showed vasodepressor activity, whereas AM-(1-31)-$NH_2$, AM-(1-25)-OH, AM-(1-21)-$NH_2$, acetyl-AM-(16-21)-$NH_2$, and acetyl-AM-(16-36)-$NH_2$ all showed vasopressor activity.

V. AM(11-22), a New, Naturally Occurring Vasopressor Peptide

This disclosure identifies vasoconstrictor compounds, in particular a vasoconstrictor peptide derived from adrenomedullin (AM), and consisting of amino acids 11-22 of this protein.

Disclosure provided herein demonstrates that AM is specifically degraded by the matrix metalloproteinase (MMP) known as MMP-2. The degradative processing of AM by MMP-2 produces specific AM digestion products that can be detected in the urine of normal individuals. Surprisingly, one of the peptide products, AM(11-22), exhibits a delayed vasoconstrictor activity in rats. In addition, it appears that this activity occurs without the peptide interacting with CRLR, RAMP2, or RAMP3 (the expected receptor components), suggesting that other independent receptor system(s) may be involved in the observed vasoconstrictor activity.

It is believed that AM (11-22) is useful as a hypertensive drug, for example to treat shock or other hypotensive conditions. Because AM(11-22) is an endogenous peptide, it is expected that this peptide will be well tolerated by subjects. In addition, it surprisingly exhibits an unusually long duration of activity (on the order of hours) in comparison to previously known AM-derived peptides. The kinetics of activity of the AM(11-22) peptide could not have been predicted from its amino acid sequence, nor from a mere comparison to previously described AM peptides. The particularly long activity duration of AM(11-22) makes it superior to prior peptides, and contributes to the promise of AM(11-22) as a useful antihypotensive agent.

The finding of a vasoconstrictor peptide as a result of the digestion of AM by MMP-2 is intriguing, and is in line with a previous study where different fragments of AM were synthesized and assayed for blood pressure regulation activity in anesthetized rats (Watanabe et al., *Biochem. Biophys. Res. Commun.* 219:59-63, 1996). Although the fragment AM(11-22) was not studied in that report, the structurally related but not identical peptide acetyl-AM(16-21) showed vasopressor activity. Another similar but distinct fragment, AM(11-26), was purified from bovine adrenal medulla but, although the peptide induced vasopressor activity, the elevation in blood pressure lasted only about 70 seconds (Kitamura et al., *Peptides* 22:1713-1718, 2001). The involvement of the catecholamine system has been suggested as a mechanism to explain the pressor activity of these particular fragments of AM (Watanabe et al., *Biochem. Biophys. Res. Commun.* 219:59-63, 1996). The delay between the administration of AM(11-22) and the onset of the vasopressor response, together with the disconnection of AM(11-22) and the AM receptor system, is consistent with the existence of an indirect mechanism responsible for the reported effects.

VII. Hypertension and Inhibitors of MMP-2

Hypertension, which refers to elevated arterial pressure, is a widespread health problem in developed countries. Diagnosis of hypertension depends on measurement of blood pressure, which is typically reported as a ratio of systolic pressure (arterial pressure during contraction of the heart muscle) to diastolic pressure (residual arterial pressure during relaxation of the heart muscle), reported in units of mmHg. A normal diastolic blood pressure is between about 60-85 mmHg. Diastolic pressures above 85 mmHg are generally diagnostic of hypertension. By some estimates, the arterial blood pressure of fifteen percent of American adults is in a hypertension range that requires medical treatment.

A number of factors have been implicated in the development of hypertension. These include heredity and a number of environmental factors such as salt intake, obesity, occupation, family size, and crowding. Additional factors which may modify the course of hypertension include age, race, sex, stress, diet, smoking, serum cholesterol, and glucose intolerance.

The effects of hypertension are numerous, with the most severe being premature death, commonly caused by heart disease related to hypertension. Hypertension imposes an increased work load on the heart; related effects on the heart include angina pectoris, increased myocardial mass or hypertrophy (enlarged heart), and, late in the disease, evidence of ischemia or infarction.

Neurologic effects of hypertension are commonly divided into retinal and central nervous system changes. With respect to retinal impact, increasing severity of hypertension is associated with focal spasm as well as hemorrhages, exudates and papilledema, which often produce scotomata, blurred vision and even blindness. Central nervous system dysfunction may cause occipital headaches, dizziness, lightheadedness, vertigo, tinnitus and dimmed vision.

Drug therapy is a common approach to treatment of hypertension. In general, antihypertensive drugs belong to one of five classes of compounds: diuretics, antiadrenergic agents, vasodilators, calcium entry blockers, and angiotensin-converting enzyme (ACE) inhibitors.

While the precise molecular pathogenesis of hypertension is not fully understood, recent studies suggest that matrix metalloproteinases (MMP) contribute to this process by remodeling the extracellular matrix (Mulvany, *News Physiol. Sci.* 17:105-109, 2002; D'Armiento, *Trends Cardiovasc. Med* 12:97-101, 2002; Intengan and Schiffrin, *Hypertension* 38:581-587, 2001). The MMP family includes more than 20 members that share structural domains but differ in substrate specificity, cellular sources, and transcriptional regulation. A common characteristic of these enzymes is their ability to degrade components of the extracellular matrix. This feature has relevance to almost every aspect of mammalian biology and pathophysiology (Brinckerhoff and Matrisian, *Nat. Rev. Mol. Cell Biol.* 3:207-214, 2002).

The inventors have surprisingly discovered that specific inhibition of MMP-2, for instance with the compound BB-94, causes marked reduction of blood pressure (see Example 2). With this knowledge, the use of MMP-2 specific inhibitors in the regulation of blood pressure, and particularly to reduce hypertensions, is now enabled.

Many inhibitors of matrix metalloproteases are known. See, for instance, the following patent and scientific publications for descriptions of specific inhibitors, classes of inhibitors, and methods of making and testing inhibitors: U.S. Pat. No. 5,831,004 (Inhibitors of Metalloproteases, Pharmaceutical Compositions Comprising Same and Methods of Their Use); U.S. Pat. No. 6,117,869 (Compounds for and Methods of Inhibiting Matrix Metalloproteinases); U.S. Pat. No. 6,265,432 (Fluorine-Substituted Biphenyl Butyric Acids and their Derivatives as Inhibitors of Matrix Metalloproteinases); U.S. Pat. No. 6,307,101 (Inhibitors of Metalloproteases, Pharmaceutical Compositions Comprising Same and Methods of Their Use); U.S. Pat. No. 6,339,160 (Metalloproteinase Inhibitors, Their Therapeutic use and Process for the Production of the Starting Compound in the Synthesis Thereof); U.S. Pat. No. 6,350,885 (Tricyclic Heteroaromatics and their Derivatives as Inhibitors of Matrix Metalloproteinases); and U.S. Pat. No. 6,133,304 (ACE Inhibitors-MMP Inhibitor Combinations); Corcoran et al., *Enzy. Prot.* 49:7-19, 1996; Kleiner and Stetler-Stevenson, *Canc. Chemother. Pharmacol.* 43 Suppl:S42-51, 1999; Kluger, *Anticancer Res.,* 19:1589-1592, 1999; Giannelli and Antonaci, *Histol. Histopathol.* 17:339-345, 2002; and Goffin et al., *Gynecol. Obstet. Invest.* 53:101-111, 2002. Specific examples of MMP-2 inhibitors include Marimastat (BB-2516) and Batimastat (BB-94) from British Biotechnology, Prinomastat (AG3340) from Aguron, Tanomastat (BAY 12-9566) from Bayer, and BMS-275291 (Bristol Meyers/Squibb). A particular contemplated natural MMP-2 inhibitor is TIMP-2 (tissue inhibitor for metalloproteinase 2), which is known to be specific for MMP-2. Though it is not absolutely necessary, it is considered beneficial that an inhibitor used in the described methods be specific (or relatively specific) for MMP-2 over other enzymes, to minimize certain possible side effects from treatment.

VIII. Pharmaceutical Compositions

The compounds described herein, including the peptide AM(11-22) and inhibitors of MMP-2, may be formulated in a variety of ways depending on the location and type of disease or condition to be treated. Pharmaceutical compositions are thus provided for both local use as well as for systemic use. The disclosure includes within its scope pharmaceutical compositions comprising AM(11-22) or an inhibitor of MMP-2 formulated for use in human or veterinary medicine.

Pharmaceutical compositions that include AM(11-22) as an active ingredient, or that include both AM(11-22) and one ore more additional active ingredients, such as vasoconstrictive or inotropic drug or antibiotic, may be formulated with an appropriate solid or liquid carrier, depending upon the particular mode of administration chosen. Additional active ingredients in provided embodiments may include, for example, norepinephrine, dopamine, or dobutamine.

In other embodiments, compositions include an inhibitor of MMP-2 as an active ingredient, or both an MMP-2 inhibitor and one ore more additional active ingredients, for instance vasodilative drugs, and may be formulated with an appropriate solid or liquid carrier, depending upon the particular mode of administration chosen.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, inhalational, topical, and oral formulations can be employed. Topical preparations can include eye drops, ointments, sprays and the like. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The pharmaceutical compositions that comprise AM(11-22) or an inhibitor of MMP-2, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

IX. Therapeutic Uses of AM(11-22)

The present disclosure includes a treatment for shock or other low blood pressure conditions in a subject such as an animal, for example a mammal, such as a laboratory animal or human subject. The method includes administering AM(11-22), or a combination of AM(11-22) and one or more other pharmaceutical agents, to the subject in a pharmaceutically compatible carrier and in an amount effective to inhibit the development or progression of a low blood pressure condition or disease.

Although the treatment can be used prophylactically in any subject in a demographic group at significant risk for shock or hypotensive conditions or diseases, subjects can also be selected using more specific criteria, such as a definitive diagnosis of the condition. For example, treatment can be initiated in a subject having signs and symptoms of shock, such as lethargy, somnolence, poor peripheral perfusion and hypotension or other hemodynamic instability. In particular examples, the clinical picture will suggest a cause for shock, such as an indwelling catheter in an immunocompromised person who is at risk of septicemia, and who may present classical signs of infection (such as fever and chills) with laboratory evidence of infection (leukocytosis with the appearance of blasts in peripheral blood samples).

The vehicle in which the drug is delivered can include pharmaceutically acceptable compositions of the drugs, using methods well known to those with skill in the art. Any of the common carriers, such as sterile saline or glucose solution, can be utilized with the drugs provided by the disclosure. Routes of administration include but are not limited to oral and parenteral routes, such as intravenous (iv), intraperitoneal (ip), rectal, topical, ophthalmic, nasal, and transdermal administration, as well as administration by inhalation.

The AM(11-22) may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* ($19^{th}$ Edition, 1995) in chapter 95.

Alternatively, AM(11-22) may be administered to the lungs of an individual, for example by inhalation through the use of a nebulizer or inhaler. In some embodiments, for example, AM(11-22) may be formulated in an aerosol, particulate, or nanoshere and drawn into the lungs using a standard nebulizer well known to those skilled in the art. In one such embodiment, AM(11-22) is conveniently delivered in the form of an aerosol spray presentation from pressurized packs or a nebulizer with the use of a suitable propellant. Suitable examples of propellants include, but are not limited to, dichlorodifluoromethane, trichlorofluoromethane, dichlorotetrafluoroethane, carbon dioxide, or any other suitable gas. In the case of a pressurized aerosol, the dosage unit can be determined by providing a valve to deliver a metered amount. In another embodiment, capsules or cartridges for use in an inhaler or insufflator can be formulated containing a powder mix of the compound and a suitable powder base such as lactose or starch. In particular embodiments, the size of the particulate, nanosphere, or aerosol droplet is optimized to target a particular lung region.

For additional descriptions of inhalation-based therapeutic application systems, see for instance Edwards D A et al. ("Large porous particles for pulmonary drug delivery," *Science* 276:1868-1871, 1997 and Valente et al. ("Recent advances in the development of an inhaled insulin product," *BioDrugs* 17:9-17, 2003).

Embodiments of other pharmaceutical compositions can be prepared with conventional pharmaceutically acceptable carriers, adjuvants, and counterions as would be known to those of skill in the art. The compositions are preferably in the form of a unit dose in solid, semi-solid and liquid dosage forms such as tablets, pills, powders, liquid solutions or suspensions.

Therapeutically effective doses of AM(11-22) can be determined by one of skill in the art, with a goal of achieving tissue concentrations that are at least as high as those achieved in the provided examples. An example of a dosage range is 0.1 to 200 mg/kg body weight orally in single or divided doses. Another example of a dosage range is 1 to 100 mg/kg body weight orally in single or divided doses. For oral administration, the compositions are, for example, provided in the form of a tablet containing 0.1 or 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated. Alternatively, dosages can be measured based on the molar amounts of the active compound. Thus, alternative dosages in some embodiments are in a range of about 0.5 nmol/kg to about 1000 nmol/kg or more, for instance 1, 1.5, 2, 4, 5, 10, 15, 20, 25, 30, 50, 75, 100, 120, 200, 400, 500 or more nmol/kg.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy. For example, severe life-threatening and prolonged hypotension with multi-organ failure may be treated more aggressively than less severe clinical presentations. Clinical responses can be assessed by a variety of parameters, such as increased blood pressure in an otherwise hypotensive individual.

X. Therapeutic Uses of Inhibitors of AM(11-22)

The present disclosure includes a treatment for hypertensive conditions in a subject such as an animal, for example a mammal, such as a laboratory animal or human subject. The method includes administering an inhibitor of AM(11-22), for instance an inhibitor that is specific for this vasoactive peptide, or a combination of an AM(11-22) inhibitor and one or more other pharmaceutical agents, to the subject in a pharmaceutically compatible carrier and in an amount effective to inhibit the condition, development or progression of hypertension. For example, other pharmaceutical agents may include one or more effective doses of another drug recognized for treatment of hypertension (such as one or more of those discussed at pages 260-269 of "Cecil Textbook of Medicine" (1992) W. B. Saunders).

Although the treatment can be used prophylactically in any subject in a demographic group at significant risk for hypertensive conditions or diseases, subjects can also be selected using more specific criteria, such as a definitive diagnosis of the condition. For example, treatment can be initiated in a subject having signs and symptoms of hypertension, which are recognized by those of ordinary skill.

The vehicle in which the drug is delivered can include pharmaceutically acceptable compositions of the drugs, using methods well known to those with skill in the art. Any of the common carriers, such as sterile saline or glucose solution, can be utilized with the drugs provided by the disclosure. Routes of administration include but are not limited to oral and parenteral routes, such as intravenous (iv), intraperitoneal (ip), rectal, topical, ophthalmic, nasal, and transdermal administration, as well as administration by inhalation.

The AM(11-22) inhibitor may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* (19th Edition, 1995) in chapter 95.

Alternatively, AM(11-22) inhibitors may be administered to the lungs of an individual, for example by inhalation through the use of a nebulizer or inhaler. In some embodiments, for example, an AM(11-22) inhibitor may be formulated in an aerosol, particulate, or nanoshere and drawn into the lungs using a standard nebulizer well known to those skilled in the art. In one such embodiment, AM(11-22) is conveniently delivered in the form of an aerosol spray presentation from pressurized packs or a nebulizer with the use of a suitable propellant. Suitable examples of propellants include, but are not limited to, dichlorodifluoromethane, trichlorofluoromethane, dichlorotetrafluoroethane, carbon dioxide, or any other suitable gas. In the case of a pressurized aerosol, the dosage unit can be determined by providing a valve to deliver a metered amount. In another embodiment, capsules or cartridges for use in an inhaler or insufflator can be formulated containing a powder mix of the compound and a suitable powder base such as lactose or starch. In particular embodiments, the size of the particulate, nanosphere, or aerosol droplet is optimized to target a particular lung region.

For additional descriptions of inhalation-based therapeutic application systems, see for instance Edwards D A et al. ("Large porous particles for pulmonary drug delivery," *Science* 276:1868-1871, 1997 and Valente et al. ("Recent advances in the development of an inhaled insulin product," *BioDrugs* 17:9-17, 2003).

Embodiments of other pharmaceutical compositions can be prepared with conventional pharmaceutically acceptable carriers, adjuvants, and counterions as would be known to those of skill in the art. The compositions are preferably in the form of a unit dose in solid, semi-solid and liquid dosage forms such as tablets, pills, powders, liquid solutions or suspensions.

Therapeutically effective doses of AM(11-22) inhibitor for use with the methods described herein are expected to be similar in many instances to already-determined effective dosages for known inhibitors. In addition, dosages can be determined by one of skill in the art, with a goal of achieving tissue concentrations that are at least as high as high as those achieved in the provided examples. An example of a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 0.1 or 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated. Alternatively, dosages can be measured based on the molar amounts of the active compound. Thus, alternative dosages in some embodiments are in a range of about 0.5 nmol/kg to about 1000 nmol/kg or more, for instance 1, 1.5, 2, 4, 5, 10, 15, 20, 25, 30, 50, 75, 100, 120, 200, 400, 500 or more nmol/kg.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy. For example, severe life-threatening and prolonged hypotension with multi-organ failure may be treated more aggressively than less severe clinical presentations. Clinical responses can be assessed by a variety of parameters, such as increased blood pressure in an otherwise hypotensive individual.

XI. Kits

The compounds disclosed herein, and in particular peptide AM(11-22) or an inhibitor of AM(11-22), can be supplied in the form of kits for use influencing blood pressure, for instance in prevention and/or other treatment of a disorder, condition or diseases (for example, shock or another hypotensive condition in the case of AM(11-22), or hypertension in the case of an inhibitor of AM(11-22)). In such a kit, a clinically effective amount of the active ingredient(s) is provided in one or more containers. The active ingredient(s) may be provided suspended in an aqueous solution or as a freeze-dried or lyophilized powder, for instance. In certain embodiments, it will be provided in the form of a pharmaceutical composition.

Kits according to certain embodiments of this disclosure can also include instructions, usually written instructions, to assist the user in treating a disorder, condition or disease (for example, treatment of hemorrhage or shock or other hypotensive condition) with the vasoconstrictor AM(11-22). Still other kits, particularly those in which an inhibitor of AM(11-22) is provided, will include instructions to assist the user in treating a disorder, condition or disease (for example, treatment of hypertension) with the AM(11-22) inhibitor. The instructions in kits can be for use of the active ingredient for any of the purposes described herein. Instructions can optionally be provided on a computer readable medium.

The container(s) in which an active ingredient, optionally with other compound(s), is supplied can be any conventional container that is capable of holding the supplied form, for instance, microfuge tubes, ampoules, or bottles. In some applications, the therapeutic compound may be provided in pre-measured single use amounts in individual, typically disposable, tubes or equivalent containers.

The amount of active ingredient (for example, AM(11-22) or an inhibitor of AM(11-22)) supplied in the kit can be any appropriate amount, depending for instance on the market to which the product is directed. For instance, if the kit is adapted for research or clinical use, the amount of vasoconstrictor compound provided would likely be an amount sufficient for several treatments.

Certain kits according to this disclosure will also include one or more other agents useful in treating shock or another hypotensive condition. For example, such kits may include one or more effective doses of other vasoconstrictive or inotropic drugs (such as norepinephrine, dopamine or dobutamine), or other agents useful in the treatment of particular conditions (such as an antibiotic in the treatment of septic shock). Still other kits will also include one or more other agents useful in treating hypertension or a hypertensive condition. For example, such kits may include one or more effective doses of other drugs recognized for treatment of hypertension (such as those discussed in "Cecil Textbook of Medicine" (1992) W. B. Saunders, at pages 260-269 (incorporated herein by reference) for instance), or other agents useful in the treatment of particular conditions.

XII. Methods of Screening for Inhibitors of AM(11-22) Activity

In certain circumstances, it is desirable to inhibit the vasoconstrictor activity of AM(11-22), for example, for the treatment of hypertension. An antihypertensive effect can be achieved by inhibiting the effect of AM(11-22) in a subject, for instance by administering an AM(11-22) inhibitor to the subject. Such an inhibitor can be identified in a screening assay for inhibitors of AM(11-22)-mediated vasoconstriction.

In general, a screening assay is carried out by determining whether a given test compound inhibits AM(11-22)-mediated vasoconstriction; inhibition of AM(11-22)-mediated vasoconstriction indicates that the test compound is an AM(11-22) inhibitor. In some embodiments, this is accomplished by exposing a blood vessel to AM(11-22) in the presence and absence of the test compound. A reduction of AM(11-22)-induced vasoconstriction, for example as measured by increased blood vessel dilation, decreased blood vessel constriction, or a reduction in blood pressure in the vessel (or, in a subject if the vessel is in a subject) indicates that the test compound is an inhibitor of AM(11-22). In some embodiments, the blood vessel is in an in vitro system (for instance, a mesenteric artery system such as that described in international application PCT/US02/26050, published as WO 03/015700), whereas in other embodiments, the blood vessel is in a subject, for example a rat or other mammal.

An AM(11-22) inhibitor can be any type of compound that is capable of opposing (inhibiting or reducing) a vasoconstrictor activity of AM(11-22), for example, an antibody (such as a monoclonal antibody), a small molecule inhibitor, or a peptide. Libraries of molecules useful for screening for inhibitors are well known to those of ordinary skill in the art. See, for instance, published international application PCT/US02/23172 (WO 03/008627; incorporated herein by reference), which describes additional methods of screening for interacting molecules and libraries adapted for such screens.

The following examples are provided to illustrate certain particular features and/or embodiments. These examples should not be construed to limit the disclosure to the particular features or embodiments described.

EXAMPLES

Example 1

Identification and Characterization of AM(11-22)

Methods

Chemicals. Synthetic human AM was purchased from Peninsula (S. Carlos, Calif.). Purified human complement factor H was obtained from Sigma (St. Louis, Mo.). Predicted AM fragments were synthesized by Princeton Biomolecules Co. (Langhorne, Pa.). Human recombinant MMP-2 and MMP-9 were obtained as described (Fridman et al., *J. Biol. Chem.* 267:15398-15405, 1992).

Digestion reactions. Synthetic AM (240 µg/reaction) was exposed to 11.5 µg MMP-2 or MMP-9 in low salt collagenase buffer (50 mM Tris, pH 7.5, 50 mM NaCl, 0.02% Brig) for different periods of time in the presence or absence of 6 mg factor H. These amounts correspond to an approximate molar ratio of 1:250:250 (enzyme:AM:factor H). The reaction was stopped with EDTA. Digestion reactions were run in 16% Tricine gels (Invitrogen, Carlsbad, Calif.) under reducing conditions and stained with Gel Code Blue Stain Reagent (Pierce, Rockford, Ill.).

High performance liquid chromatography (HPLC). Digestion reactions were also loaded into an analytical reverse phase R2H 5×100 mm HPLC column (Poros, Applied Biosystems, Foster City, Calif.) in a 10-60% acetonitrile gradient over 10 minutes and the protein peaks eluted from the column were detected with a wavelength of 230 nm.

Mass spectrometry. The protein peaks identified by HPLC were further characterized by mass spectrometry. 1 µl of each HPLC fraction was mixed with 1 µl of α-cyano4-hydroxycinnamic acid. 1 µl of each mixture was applied to a MALDI plate and allowed to air dry. The plate was loaded into a PerSeptive Biosystems Voyage DE mass spectrometer (ABI, Foster City, Calif.). The instrument was calibrated with angiotensin I using a two-point calibration, angiotensin I at 1296.7 m/z and the matrix dimer at 379.0 m/z. The laser intensity utilized to observe the peptides was 2721 with an accelerating voltage of 25,000 volts. The extraction delay time was 50 nsec. 100 laser shots comprised a spectrum. The resulting data were analyzed using Voyager Data Explorer (ABI).

Figure 3:
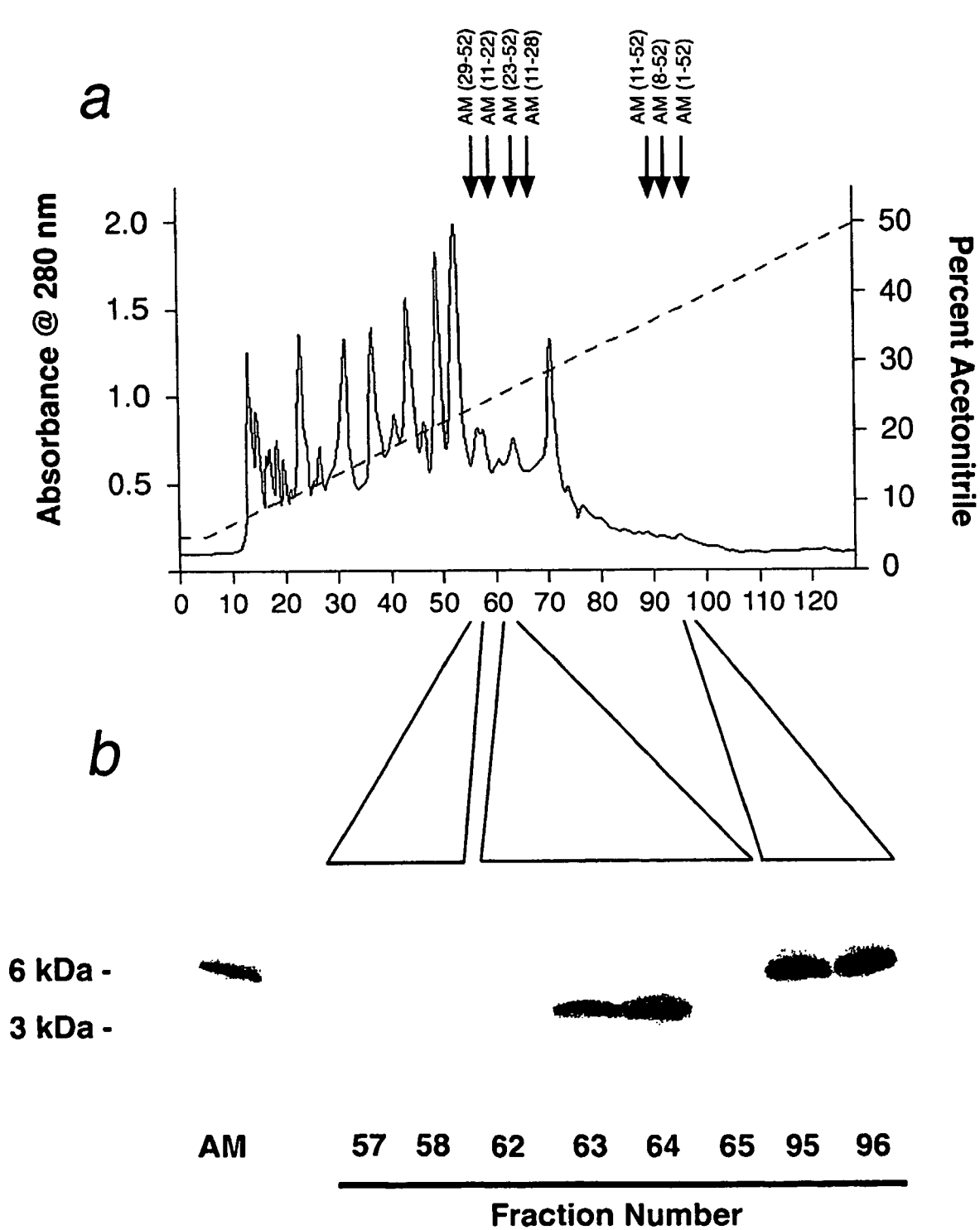
FIG. 3 illustrates that urine from normal volunteers contains products of MMP-2-dependent AM degradation. After an initial C-18 cartridge extraction, the equivalent of 250 ml of urine was fractionated through a C-18 HPLC preparative column following an acetonitrile gradient (dotted line). Select fractions were loaded into a 12% polyacrylamide gel, transferred into nitrocellulose, labeled with a polyclonal antibody against AM, and developed by chemiluminescence. Synthetic AM (3 ng) was added in the first lane as a positive control.

Detection of AM fragments in urine. Urine (250 ml) from healthy male volunteers was extracted through C-18 Sep-Pak cartridges (Waters Corporation, Milford, Mass.). The eluate was freeze dried, resuspended in 5 ml 5% acetonitrile in water+0.1% trifluoroacetic acid and fractionated by HPLC in a C-18 preparative column (Delta Pack 30 mm×30 cm, Waters Corporation) using a 5-60% acetonitrile gradient over 155 minutes, at a flow rate of 15 ml/minute. The column had been previously standardized with the synthetic peptides (FIG. 3A). Fractions were freeze dried, resuspended in sample buffer (Invitrogen) and run in 12% Bis-Tris gels (Invitrogen) under reducing conditions. Peptides were transferred into nitrocellulose filters and western blotting was performed with a previously characterized antibody against AM is and a chemiluminescence kit (ECL+plus Western Blotting Detection System, Amersham Biosciences, Piscataway, N.J.).

Blood pressure measurements. Male 10-week-old Lewis/ssncr rats (SAIC, Frederic, Md.) were anesthetized with 3% halothane, intubated, and maintained with 1% halothane in 70% nitrous oxide and 30% oxygen (VMS Anesthesia Machine, Matrx, Medical Inc., Orchard Park, N.Y.) at 82 strokes/minute. Rectal temperature was monitored through the experiment. A PE50 catheter was placed on the right femoral artery and arterial blood pressure was recorded through a P23XL transducer (Grass Instruments, Quincy, Mass.). Peptides were injected into the right femoral vein through another catheter. To confirm that changes in blood pressure were not an artifact of the anesthesia, the experiments were repeated in conscious animals. After catheters were placed under anesthesia, the animals were allowed to recover for 24-48 hours before taking blood pressure measurements. All procedures were performed under a protocol approved by the National Institutes of Health.

Measurement of cAMP response. The rat fibroblast cell line Rat2 was obtained from the American Tissue Culture Collection (Manassas, Va.) and kept in RPMI-1640 medium supplemented with 10% fetal calf serum (Invitrogen). Accumulation of intracellular cAMP was measured as described (Pío et al., *J. Biol. Chem.* 276:12292-12300, 2001). Cells were seeded in 24-well plates at $2 \times 10^4$ cells/well and incubated at 37° C. in 5% $CO_2$ until they reached 80% confluency. Before the assay, cells were incubated for 15 minutes in TIS medium (RPMI-1640 plus 10 µg/ml transferrin, 10 µg/ml insulin, and 50 nM sodium selenite) containing 1% bovine serum albumin, 1 mg/ml bacitracin, and 100 µM isobutylmethylxanthine. Peptides were applied in the same medium for 5 minutes at the indicated concentrations in a volume of 250 µl. The reaction was terminated by adding an equal volume of ice-cold ethanol. cAMP contents were measured using the Biotrac cAMP radioimmunoassay (Amersham).

Results

AM is a Substrate for MMP-2

MMP-2 rapidly cleaves synthetic AM in a time-dependent manner as demonstrated by the progressive appearance of lower molecular weight bands in polyacrylamide gels (FIG. 1, lanes 1-4). The resistance of AM to degradation by MMP-9 (FIG. 1, lanes 9-12) underscores the specificity of MMP-2-predicted degradation, considering that both enzyme preparations (MMP-2 and MMP-9) are able to efficiently digest a variety of common substrates, including gelatin and thiol peptolide. Complement factor H, the serum binding protein for AM (Pío et al., *J. Biol. Chem.* 276: 12292-12300, 2001), is not a substrate for either one of the MMPs, but addition of factor H completely prevents MMP-2-mediated degradation of AM (FIG. 1, lanes 5-8). In contrast, factor H does not interfere with the ability of MMP-2 to degrade thiol peptolide, demonstrating that prevention of AM degradation by MMP-2 is dependent on the specific protein-protein interaction between AM and factor H.

Analysis of these digestion reactions by reverse-phase chromatography reveals a rapid decrease in the area of the peak representing the intact peptide (arrow in FIG. 2A) and the concomitant progressive appearance of additional new peaks (FIGS. 2B-2E). Mass spectrometry analysis identifies the AM fragments generated by MMP-2 digestion. These include AM(8-52), AM(11-52), AM(23-52), AM(29-52), AM(11-28), and AM(11-22). The amino acid patterns at the cleavage sites are compatible with the predicted motifs for MMP-2 targets (Turk et al., *Nature Biotechnol.* 19:661-667, 2001). Two of the AM cleavage peptides, AM(8-52) and AM(11-52), maintain both the intramolecular ring structure and the α-amide, two characteristics required for AM receptor activation (Eguchi et al., *Endocrinology* 135:2454-2458, 1994). Two other fragments, AM(23-52) and AM(29-52), retain only the terminal amide; whereas the remaining two, AM(11-28) and AM(11-22), have the loop but not the carboxy end of the molecule. Each of these peptides was synthesized to further characterize their biological activities.

Predicted Fragments of MMP-2-digested AM are Found in vivo

To investigate whether some of the fragments obtained by in vitro digestion of AM are also present in a biological fluid, urine samples from healthy human volunteers were assayed for signature AM peptide fragments generated by MMP-2 cleavage. Urine is an abundant source for both MMP-2 (Thrailkill et al., *Pediatr. Nephrol.* 13:223-229, 1999) and AM (López and Martínez, *Int. Rev. Cytol.* 221:1-92, 2002). First, a preparative C-18 HPLC column was standardized using the synthetic peptides as markers and identified the fractions in which particular peptides eluted off the column (FIG. 3A). Using the same conditions, the equivalent of 250 ml of urine was fractionated and selected fractions analyzed by Western blotting with a well characterized antibody against AM (Martínez et al., *Endocrinology* 136:4099-4105, 1995).

Chemiluminescent detection revealed a moiety of approximately 6 kDa that co-migrates with synthetic AM in fractions 95 and 96, and smaller fragments in fractions 57, 58, 63, and 64 (FIG. 3B). Comparison of these results with the elusion profile of the synthetic peptides identifies the light band observed in fractions 57 and 58 as AM(29-52), the one in fractions 63 and 64 as AM(23-52), and the larger peptide of fractions 95 and 96 as undigested AM. Since the detection antibody employed recognizes the carboxy end of AM (Martínez et al., *Endocrinology* 136:4099-4105, 1995), only the fragments containing this region were detected by Western blot analysis.

Peptide Fragments Exhibit Both Hypotensive and Hypertensive Activity

Vasodilatation is the best characterized function of AM (López and Martínez, *Int. Rev. Cytol.* 221:1-92, 2002; Eto, *Peptides* 22:1693-1711, 2001). To understand the physiological implications of the digestion of AM by MMP-2, the impact of the AM fragments on blood pressure regulation in rats was studied.

Figure 4:
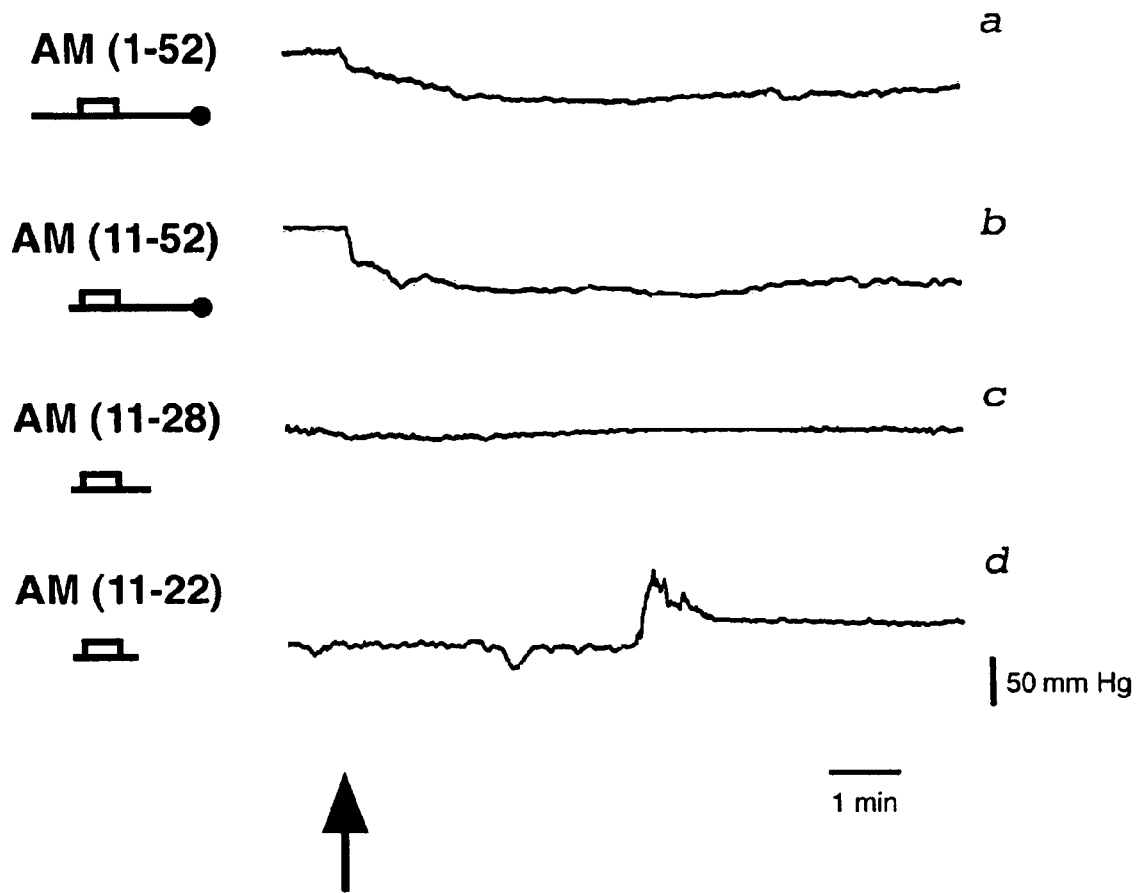
FIGS. 4A, 4B, 4C, and 4D are a series of blood pressure recordings, showing that one of the newly identified AM fragments elevates blood pressure in rats. Typical recordings of the blood pressure modifications elicited by intact AM (FIG. 4A) and its fragments (FIGS. 4B, 4C, and 4D) in anesthetized rats. The peptides AM(8-52) and AM(11-52) induced hypotension and only the effect of the second is shown (FIG. 4B). The fragments AM(23-52), AM(29-52), and AM(11-28) did not have any effect and only the diagram of the latest is shown (FIG. 4C). The small peptide AM(11-22) induced vasoconstriction several minutes after injection (FIG. 4D). The arrow indicates the time when the peptides were injected. The horizontal bar represents one minute. The vertical bar represents 50 mm Hg. Schematic drawings of the structure of the AM peptides are provided underneath their denomination. The solid circle represents the amide group at the carboxy end and the rectangle indicates the intramolecular disulfide bond.

Untreated animals had a systolic blood pressure of 125±10 mm Hg (n=5). Intact AM (FIG. 4A) and the peptide fragments containing both the intramolecular loop and the final tyrosine-amide (FIG. 4B) induce a deep and long-lasting hypotension (reduction of 55±5 mm Hg, n=5). In contrast, AM(23-52), AM(29-52), and AM(11-28) do not have any discernible effect on blood pressure regulation (FIG. 4C).

Surprisingly, the fragment AM(11-22) shows a vasopressor effect (71±24 mm Hg over basal levels, n=5, FIG. 4D), indicating that MMP-2 degradation of AM not only attenuates the hypotensive effect of AM but that it also generates a hypertensive fragment.

The hypotensive and hypertensive AM peptides exhibit very different modes of action, with the vasodilator molecules acting almost immediately following injection, and the vasoconstrictor peptide needing 4 to 5 minutes before eliciting its effect. Though not intending to be limited to any one explanation, this divergence in timing suggests that AM(11-22) may be acting through a receptor system independent of the one used by AM and the larger peptide fragments.

The synthetic peptides induced similar blood pressure changes in anesthetized as well as in conscious animals, indicating that the above observations are not an artifact of anesthesia.

The Vasoconstrictor Peptide Does Not Act Via a Classic AM Receptor Mechanism

To determine if AM peptide fragments elicit their hypotensive and hypertensive effects via the AM receptor, their cAMP response in fibroblasts was examined. Rat2 is a fibroblast cell line that contains a well characterized AM receptor that does not bind other members of the AM peptide family, such as calcitonin gene-related peptide (CGRP) (Coppock et al., *Biochem. J.* 338:15-22, 1999).

Figure 5A:
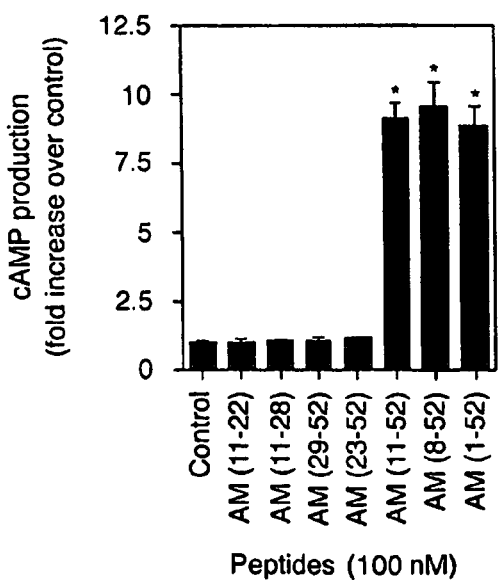
FIGS. 5A and 5B are a pair of bar graphs showing that some AM digestion products are no longer able to activate the AM receptor. Intracellular levels of cyclic adenosine monophosphate (cAMP) were quantified by radioimmunoassay as an indirect measurement of AM receptor activation in Rat2 cells.

AM(8-52) and AM(11-52) elicit an intracellular elevation of cAMP in Rat2 cells equal to the one induced by the intact AM molecule, whereas the rest of the fragments do not elevate cAMP levels over basal values (FIG. 5A). These observations confirm a previous report that indicated loss of either the disulfide bond or the terminal amide results in inability of receptor binding (Eguchi et al., *Endocrinology* 135:2454-2458, 1994).

Figure 5B:
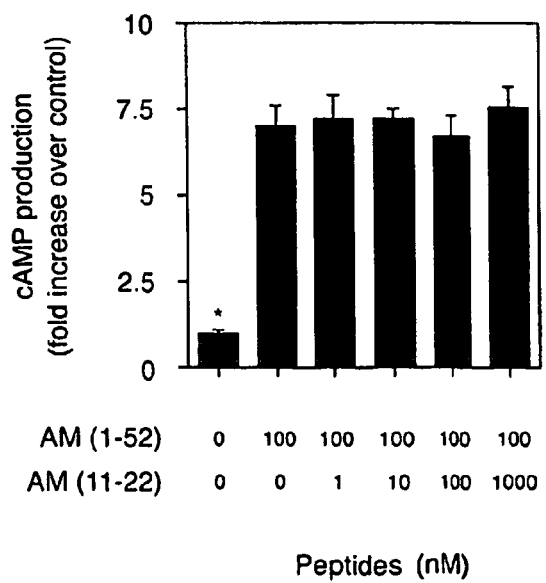
Figure 6:
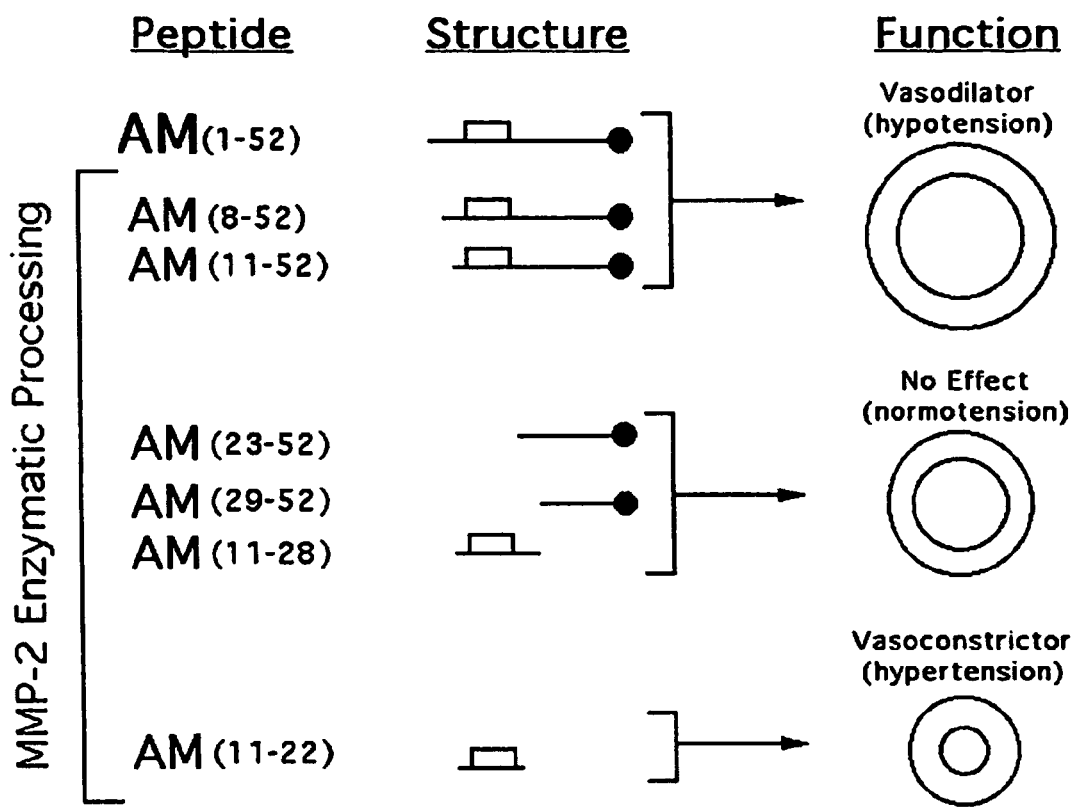
FIG. 6 is a diagram of the sequential degradation of AM into smaller peptides and the physiological implications of the process. The larger peptides maintain the vasodilator capability characteristic of intact AM, whereas intermediate peptides lack vasomotor activity, and the small peptide AM(11-22) surprisingly is a vasoconstrictor. Structural diagrams are as in FIG. 4.

Whether the peptides that do not elicit a cAMP response are in fact competitors for AM binding to its receptor was also studied. This seems not to be the case, since increasing concentrations of these peptides do not have any effect on the induction of the cAMP response by AM, as exemplified by AM(11-22) (FIG. 5B). This is also compatible with the vasoconstrictor activity of AM(11-22) being mediated through a different receptor system.

Discussion

Here it is shown that AM is rapidly cleaved by MMP-2 and that as a result smaller peptides are sequentially produced. The specificity of the cleavage reaction was demonstrated by the fact that another gelatinase, MMP-9, did not affect AM integrity. Interestingly, the AM binding protein complement factor H efficiently blocked MMP-2 degradation of AM while it did not inhibit catabolism of other MMP-2 substrates. Factor H was not a substrate for MMP-2 either.

Unique peptide fragments, consistent with MMP-2-mediated degradation of AM, were found in a biological fluid, suggesting that the in vivo catabolism of AM is predicted, at least in part, by MMP-2 activity.

The peptide products that retained the amidated end of the molecule and the internal disulfide loop induced vasodilatation in vivo and elevated cAMP levels in a cell line known to express the specific AM receptor, whereas peptides lacking either of these features did not.

The smallest peptide fragment (AM(11-22)), which contains little more than the internal loop, elicited a hypertensive response without influencing AM receptor activation. These observations suggest that MMP-2 activity may contribute to the hypertensive phenotype both by reducing the levels of the potent vasodilator AM and by generating a new hypertensive peptide.

In a previous study, Lewis and colleagues exposed synthetic human AM to cell membrane preparations from ovine kidney, adrenal, and lung tissues (Lewis et al., *Peptides* 18:733-739, 1997). Among the series of peptide fragments generated in this manner, one of the most abundant was AM(8-52), which has also been found as one of the first products resulting from MMP-2-mediated degradation. In the discussion of that article, the authors predicted the need for metalloproteinase and an aminopeptidase activities to explain all the fragmentary peptide products they found.

It has previously been reported that complement factor H enhances AM function in several experimental model systems such as induction of cAMP in Rat2 fibroblasts (Pío et al., *J. Biol. Chem.* 276:12292-12300, 2001), growth promotion of breast cancer cell lines (Pío et al., *J. Biol. Chem.* 276:12292-12300, 2001), and reduction of insulin secretion by rat isolated pancreatic islets (Martínez et al., *J. Endocrinol.* 170:503-511, 2001). It was also determined that this enhancing effect was not due to changes in the kinetics of AM binding to its receptor (Pío et al., *J. Biol. Chem.* 276:12292-12300, 2001).

Here, it is shown that factor H is able to completely prevent the degradation of AM by MMP-2, therefore defining a mechanism by which the binding protein prolongs the half life of AM and thus increases its biological effects. This regulatory process may be very relevant to understand the biology of AM in regulating vascular tone. Current radioimmunoassay protocols used to determine the circulating levels of AM require a preliminary purification step through a C-18 cartridge. An unanticipated consequence of this step is the removal of factor H and the fraction of AM that is bound to it. As a result, existing protocols measure only free AM and the reported concentrations are extremely low, varying from 1 to 10 picomolar (López and Martínez, *Int. Rev. Cytol.* 221:1-92, 2002). Obviously, these levels are insufficient for receptor activation and have raised doubts about the endocrine effects of AM. On the other hand, the existence of a serum AM binding protein which circulates at a high concentration (500 µg/ml) (Whaley and Ruddy, *J. Exp. Med.* 144:1147-1163, 1976) and protects AM from proteolytic degradation suggests that the most important pool of AM may be the one that circulates bound to factor H rather than the free fraction.

There are precedents where MMP-2 can cleave other vasoactive substances as well. For instance, this enzyme digests the vasoconstrictor big endothelin-1, ET-1(1-38), yielding the smaller peptide ET-1(1-32) which is also a vasoconstrictor (Fernandez-Patron et al., *Circ. Res.* 85:906-911, 1999). Furthermore, CGRP is also degraded by MMP-2 but, in contrast with our observations on AM, the resulting vasoconstriction is just a consequence of the reduction in the levels of the vasodilator CGRP (Fernandez-Patron et al., *Circ. Res.* 87:670-676, 2000).

The ability of MMP-2 to radically change the physiological action of a substrate has been demonstrated before in the case of monocyte chemoattractant protein-3 (MCP-3). Full length MCP-3 induces chemotaxis of mononuclear inflammatory cells, but the cleavage products act as general chemokine antagonists and dampen inflammation (McQuibban et al., *Science* 289:1202-1206, 2000).

MMP-2 is also a neutral endopeptidase and investigators are intensively studying clinical applications for inhibitors of this enzyme family (Nawarskas et al., *Heart Dis.* 3:378-385, 2001; Corti et al., *Circulation* 104:1856-1862, 2001). There is evidence that three different neutral endopeptidase inhibitors (candoxatrilat, thiorphan, and SCH32615) enhance clinical aspects attributed to AM (Lisy et al., *Am. J. Physiol. Renal Physiol.* 44:F410-F414, 1998; Wilkinson et al., *Br. J. Clin. Pharmacol.* 52:159-164, 2001; Rademaker et al., *Hypertension* 39:93-98, 2002). Whether this enhancement is due to MMP-2 blockade or to other endopeptidases remains to be determined. Specific inhibitors of MMPs are being used to prevent extracellular matrix remodeling in cardiovascular diseases, with encouraging results (Creemers et al., *Circ. Res.* 89:201-210, 2001). The observation provided herein that MMP-2-mediated digestion of AM generates a vasoconstrictor out of the original vasodilator peptide defines a new mechanism by which MMP-2 further contributes to regulation of vasomotor tone, and first suggested that application of MMP-2 inhibitors could be an attractive drug target to regulate blood pressure.

Example 2

Inhibitors of MMP-2 Can Be Used as Hypertensive Agents

This example demonstrates that inhibitors of MMP-2, such as BB-94, can be used as hypertensive agents to influence blood pressure and to treat or reduce the effects of shock and other hypotensive conditions.

It is shown above in Example 1 that MMP-2 degrades adrenomedullin (AM) into smaller peptides, resulting in an increase of blood pressure in rats due to the loss of hypotensive peptides (adrenomedullin and the longer AM-derived peptides) and the generation of hypertensive peptide AM(11-22).

To further demonstrate that this processing occurs in vivo, an MMP-2 inhibitor (BB-94) was administered to hypertensive SHR rats while measuring their arterial blood pressure using methods essentially as described in Example 1. Specifically, 5 mg of BB-94 (2.5 mg/ml in PBS H 7.4 with 0.1% Tween-20) was injected IP into rats, and blood pressure was monitored as described above.

Figure 7:
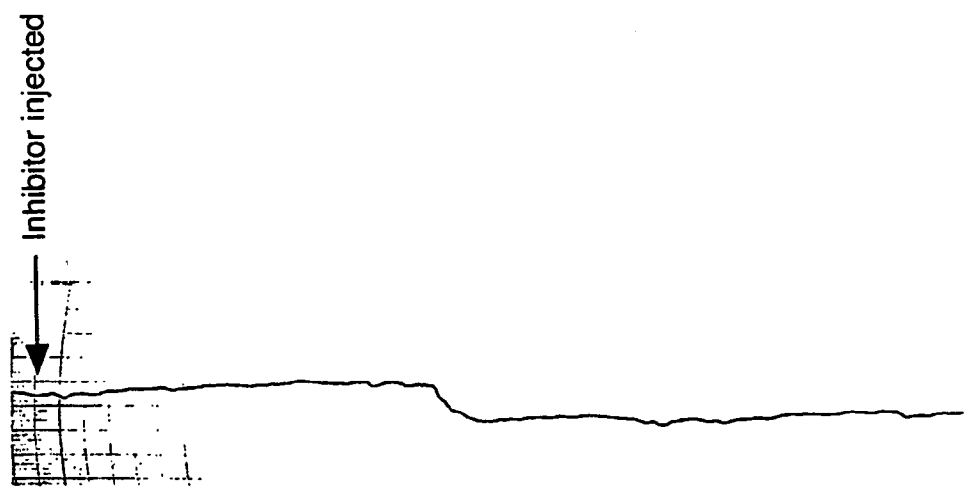
FIG. 7 shows a typical recording of the blood pressure modification in a rat, provided by injecting a rat with BB-94, a specific inhibitor of MPP-2 activity. Rats were injected intraperitoneally (IP) with 5 mg of BB-94 (2.5 mg/ml in PBS H 7.4 with 0.1% Tween-20); a typical chart of blood pressure is shown. Each block on the chart is one minute; though the drop in blood pressure began 20 minutes after the drug was introduced, the decreased blood pressure effects were measurable to at least three hours after injection.

FIG. 7 shows that, 20 minutes after injection of the inhibitor, the blood pressure in the animal dropped about 80 mm of Hg and remained at that level for at least 2.5 hours.

It is believed that this finding further provides evidence that MMP-2 digests AM in vivo, and this phenomenon induces hypertension. Specific inhibitors of MMP-2 are therefore believed to be useful as hypotensive drugs, for instance in the treatment of hypertensive conditions, both acute and chronic.

Example 3

Expression of AM(11-22) Peptide

The expression and purification of the AM(11-22) peptide by standard laboratory techniques is now enabled. Purified AM(11-22) peptide may be used for functional analyses, antibody production, diagnostics, and therapy, for instance. Methods for expressing large amounts of protein or peptide from a cloned nucleic acid introduced into *Escherichia coli* (*E. coli*) may be utilized for the purification, localization and functional analysis of proteins; also, production of AM(11-22) can be carried out by generating full length AM (or a fragment longer than AM(11-22)), followed by specific proteolytic cleavage to produce the desired peptide.

For example, fusion proteins consisting of amino terminal peptides encoded by a portion of the *E. coli* lacZ or trpE gene linked to AM peptides may be used to prepare polyclonal and monoclonal antibodies against these proteins. Thereafter, these antibodies, or commercially available α-AM antibodies, may be used to purify proteins by immunoaffinity chromatography, in diagnostic assays to quantitate the levels of protein or peptide, and to localize peptides in tissues and individual cells by immunofluorescence. Such antibodies may be specific for epitope tags, which can be added to the expression construct for identification and/or purification purposes.

Intact native peptide, or full length AM, may also be produced in *E. coli* in large amounts, for instance for functional studies or as the starting material for proteolytic production of AM peptides. Methods and plasmid vectors for producing fusion proteins and intact native proteins in bacteria are described in Sambrook et al. (Sambrook et al., In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J*. 2:1791, 1983), pEX1-3 (Stanley and Luzio, *EMBO J*. 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). Neo-PAP fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244: 1313-1317, 1989), invertebrates, plants, and animals (Pursel et al., *Science* 244:1281-1288, 1989), which cells or organisms are rendered transgenic by the introduction of a heterologous AM encoding sequence.

For expression in mammalian cells, the encoding sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with nucleic acid amplification.

An AM-encoding sequence, such as the cDNA sequence (or portions derived from it) or a mini gene (a cDNA with an intron and its own promoter), may be introduced into eukaryotic expression vectors by conventional techniques. These vectors are designed to permit the transcription of the encoding sequence in eukaryotic cells by providing regulatory sequences that initiate and enhance the transcription and ensure its proper splicing (where the construct includes introns) and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the AM protein or peptide can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses, such as papilloma (Sarver et al., *Mol. Cell Biol.* 1:486-496, 1981) or Epstein-Barr (Sugden et al., Mol. Cell Biol. 5:410-413, 1985). Alternatively, one can also produce cell lines that have integrated the vector into genomic DNA. Both of these types of cell lines produce the gene product on a continuous basis. One can also produce cell lines can also produced that have amplified the number of copies of the vector (and therefore of the cDNA as well) to create cell lines that can produce high levels of the gene product (Alt et al., *J. Biol. Chem.* 253:1357-1370, 1978).

The transfer of DNA into eukaryotic, in particular human or other mammalian cells, is now a conventional technique. Recombinant expression vectors can be introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Felgner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the encoding sequence, such as a cDNA or one or more fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Techniques of use in packaging long transcripts can be found in Kochanek et al. (*Proc. Natl. Acad. Sci. USA* 93:5731-5739, 1996) Parks et al. (*Proc. Natl. Acad. Sci. USA* 93:13565-13570, 1996) and Parks and Graham (*J. Virol.* 71:3293-3298, 1997). AM or AM peptide encoding sequences can also be delivered to target cells in vitro via non-infectious systems, for instance liposomes.

Using the above techniques, expression vectors containing an AM encoding sequence or cDNA, or fragments or variants or mutants thereof, can be introduced into human cells, mammalian cells from other species or non-mammalian cells, as desired. The choice of cell is determined by the purpose of the treatment. For example, monkey COS cells (Gluzman, *Cell* 23:175-82, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

Embodiments described herein thus encompass recombinant vectors that comprise all or part of an AM encoding sequence, for expression in a suitable host. The AM peptide-encoding DNA is operatively linked in the vector to an expression control sequence in the recombinant DNA molecule so that the AM polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with a vector, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant AM DNA sequences and peptides, similar systems are employed to express and produce the mutant product.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the following claims:

The invention claimed is:

1. A method of vasoconstricting blood vessels in a subject, comprising:
   (a) selecting a subject in need of vasoconstriction; and
   (b) administering to the subject a therapeutically effective amount of peptide consisting of the peptide AM(11-22) (SEQ ID NO: 4) sufficient to induce vasoconstriction, thereby vasoconstricting blood vessels in the subject.

2. The method of claim 1, wherein the method of vasoconstricting blood vessels comprises administering the peptide consisting of the peptide AM(11-22) (SEQ ID NO: 4) to a subject experiencing or at risk of experiencing shock.

3. The method of claim 1, wherein the method comprises administering the peptide consisting of the peptide AM(11-22) (SEQ ID NO: 4) to a subject experiencing or at risk of experiencing vasodilatory shock.

4. The method of claim 1, wherein the method comprises administering the peptide consisting of the peptide AM(11-22) (SEQ ID NO: 4) to a subject experiencing or at risk of experiencing septic shock.

5. A pharmaceutical composition comprising a therapeutically effective amount of the peptide consisting of the peptide AM(11-22) (SEQ ID NO: 4).

6. A kit for vasoconstricting blood vessels in a subject comprising a container and an amount of the pharmaceutical composition of claim 5.

7. The kit of claim 6, further comprising a container comprising another vasoconstrictive, inotropic, or antibiotic agent.

8. The kit of claim 6, wherein the vasoconstrictive or inotropic agent is norepinephrine, dopamine, or dobutamine.

9. The kit of claim 6, further comprising instructions for administering the compound to a subject.

10. A method of screening for an inhibitor of peptide consisting of the peptide AM(11-22) (SEQ ID NO: 4), comprising:
    (a) selecting a compound; and
    (b) determining whether the compound inhibits AM(11-22)-mediated vasoconstriction, wherein inhibition of AM(11-22)-mediated vasoconstriction indicates that the compound is an inhibitor of the peptide AM(11-22) (SEQ ID NO: 4), thereby screening for the inhibitor of the peptide consisting of the peptide AM(11-22) (SEQ ID NO: 4).

11. The method of claim 10, comprising contacting a blood vessel with the peptide consisting of the peptide AM(11-22) (SEQ ID NO: 4) in the presence and absence of the compound.

12. The method of claim 11, wherein the blood vessel is in a subject.

13. The method of claim 11, wherein the subject is a rat.

14. The method of method of claim 10, wherein the compound is an antibody.

15. The method of claim 14, wherein the antibody is a monoclonal antibody.

16. The method of claim 10, wherein the compound is a peptide.

17. A method of vasodilating blood vessels in a subject, comprising:
    (a) selecting a subject in need of vasodilation; and
    (b) administering to the subject a therapeutically effective amount of an inhibitor of a vasoconstricting activity of peptide consisting of the peptide AM(11-22) (SEQ ID NO: 4) sufficient to induce vasodilation, thereby vasodilating blood vessels in the subject.

18. The method of claim 17, wherein the method of vasodilating blood vessels comprises administering the inhibitor of the peptide consisting of the peptide AM(11-22) (SEQ ID NO: 4) to a subject experiencing or at risk of experiencing hypertension.

19. The method of claim 17, wherein the inhibitor of the peptide consisting of the peptide AM(11-22) (SEQ ID NO: 4) is an antibody-or a peptide.

20. A kit for vasoconstricting blood vessels in a subject comprising a container and an amount of an inhibitor of the peptide consisting of the peptide AM(11-22) (SEQ ID NO: 4).

21. The kit of claim 20, further comprising a container comprising another vasodilative agent.

22. The kit of claim 20, further comprising instructions for administering the compound to subject.

* * * * *

SEQUENCE LISTING

```
<160> NUMBER OF SEQ ID NOS: 4

<210> SEQ ID NO 1
<211> LENGTH: 1449
<212> TYPE: DNA
<213> ORGANISM: Homo sapiens
<220> FEATURE:
<221> NAME/KEY: CDS
<222> LOCATION: (157)..(714)

<400> SEQUENCE: 1
ctggatagaa cagctcaagc cttgccactt cgggcttctc actgcagctg ggcttggact        60
tcggagtttt gccattgcca gtgggacgtc tgagactttc tccttcaagt acttggcaga      120
tcactctctt agcagggtct gcgcttcgca gccggg atg aag ctg gtt tcc gtc       174
                                      Met Lys Leu Val Ser Val
                                      1               5 gcc ctg atg tac ctg ggt tcg ctc gcc ttc cta ggc gct gac acc gct        222
Ala Leu Met Tyr Leu Gly Ser Leu Ala Phe Leu Gly Ala Asp Thr Ala
        10                  15                  20
```

| | | | | | | | | | | | | | | | |
|---|---|---|---|---|---|---|---|---|---|---|---|---|---|---|---|
| cgg | ttg | gat | gtc | gcg | tcg | gag | ttt | cga | aag | aag | tgg | aat | aag | tgg gct | 270 |
| Arg | Leu | Asp | Val | Ala | Ser | Glu | Phe | Arg | Lys | Lys | Trp | Asn | Lys | Trp Ala | |
| | | 25 | | | | 30 | | | | | 35 | | | | |

| | | | | | | | | | | | | | | | |
|---|---|---|---|---|---|---|---|---|---|---|---|---|---|---|---|
| ctg | agt | cgt | ggg | aag | agg | gaa | ctg | cgg | atg | tcc | agc | agc | tac | ccc acc | 318 |
| Leu | Ser | Arg | Gly | Lys | Arg | Glu | Leu | Arg | Met | Ser | Ser | Ser | Tyr | Pro Thr | |
| | 40 | | | | | 45 | | | | | 50 | | | | |

| | | | | | | | | | | | | | | | |
|---|---|---|---|---|---|---|---|---|---|---|---|---|---|---|---|
| ggg | ctc | gct | gac | gtg | aag | gcc | ggg | cct | gcc | cag | acc | ctt | att | cgg ccc | 366 |
| Gly | Leu | Ala | Asp | Val | Lys | Ala | Gly | Pro | Ala | Gln | Thr | Leu | Ile | Arg Pro | |
| 55 | | | | | 60 | | | | | 65 | | | | | 70 |

| | | | | | | | | | | | | | | | |
|---|---|---|---|---|---|---|---|---|---|---|---|---|---|---|---|
| cag | gac | atg | aag | ggt | gcc | tct | cga | agc | ccc | gaa | gac | agc | agt | ccg gat | 414 |
| Gln | Asp | Met | Lys | Gly | Ala | Ser | Arg | Ser | Pro | Glu | Asp | Ser | Ser | Pro Asp | |
| | | | 75 | | | | | 80 | | | | | 85 | | |

| | | | | | | | | | | | | | | | |
|---|---|---|---|---|---|---|---|---|---|---|---|---|---|---|---|
| gcc | gcc | cgc | atc | cga | gtc | aag | cgc | tac | cgc | cag | agc | atg | aac | aac ttc | 462 |
| Ala | Ala | Arg | Ile | Arg | Val | Lys | Arg | Tyr | Arg | Gln | Ser | Met | Asn | Asn Phe | |
| | | | 90 | | | | | 95 | | | | | 100 | | |

| | | | | | | | | | | | | | | | |
|---|---|---|---|---|---|---|---|---|---|---|---|---|---|---|---|
| cag | ggc | ctc | cgg | agc | ttt | ggc | tgc | cgc | ttc | ggg | acg | tgc | acg | gtg cag | 510 |
| Gln | Gly | Leu | Arg | Ser | Phe | Gly | Cys | Arg | Phe | Gly | Thr | Cys | Thr | Val Gln | |
| | | 105 | | | | | 110 | | | | | 115 | | | |

| | | | | | | | | | | | | | | | |
|---|---|---|---|---|---|---|---|---|---|---|---|---|---|---|---|
| aag | ctg | gca | cac | cag | atc | tac | cag | ttc | aca | gat | aag | gac | aag | gac aac | 558 |
| Lys | Leu | Ala | His | Gln | Ile | Tyr | Gln | Phe | Thr | Asp | Lys | Asp | Lys | Asp Asn | |
| | 120 | | | | | 125 | | | | | 130 | | | | |

| | | | | | | | | | | | | | | | |
|---|---|---|---|---|---|---|---|---|---|---|---|---|---|---|---|
| gtc | gcc | ccc | agg | agc | aag | atc | agc | ccc | cag | ggc | tac | ggc | cgc | cgg cgc | 606 |
| Val | Ala | Pro | Arg | Ser | Lys | Ile | Ser | Pro | Gln | Gly | Tyr | Gly | Arg | Arg Arg | |
| 135 | | | | | 140 | | | | | 145 | | | | | 150 |

| | | | | | | | | | | | | | | | |
|---|---|---|---|---|---|---|---|---|---|---|---|---|---|---|---|
| cgg | cgc | tcc | ctg | ccc | gag | gcc | ggc | ccg | ggt | cgg | act | ctg | gtg | tct tct | 654 |
| Arg | Arg | Ser | Leu | Pro | Glu | Ala | Gly | Pro | Gly | Arg | Thr | Leu | Val | Ser Ser | |
| | | | 155 | | | | | 160 | | | | | 165 | | |

| | | | | | | | | | | | | | | | |
|---|---|---|---|---|---|---|---|---|---|---|---|---|---|---|---|
| aag | cca | caa | gca | cac | ggg | gct | cca | gcc | ccc | ccg | agt | gga | agt | gct ccc | 702 |
| Lys | Pro | Gln | Ala | His | Gly | Ala | Pro | Ala | Pro | Pro | Ser | Gly | Ser | Ala Pro | |
| | | | 170 | | | | | 175 | | | | | 180 | | |

| | | | | |
|---|---|---|---|---|
| cac | ttt | ctt | tag gatttaggcg cccatggtac aaggaatagt cgcgcaagca | 754 |
| His | Phe | Leu | | |
| | | 185 | | |

| | |
|---|---|
| tcccgctggt gcctcccggg acgaaggact tcccgagcgg tgtggggacc gggctctgac | 814 |
| agccctgcgg agaccctgag tccgggaggc accgtccggc ggcgagctct ggctttgcaa | 874 |
| gggcccctcc ttctgggggc ttcgcttcct tagccttgct caggtgcaag tgccccaggg | 934 |
| ggcggggtgc agaagaatcc gagtgtttgc caggcttaag gagaggagaa actgagaaat | 994 |
| gaatgctgag accccggag cagggtctg agccacagcc gtgctcgccc acaaactgat | 1054 |
| ttctcacggc gtgtcacccc accagggcgc aagcctcact attacttgaa ctttccaaaa | 1114 |
| cctaaagagg aaaagtgcaa tgcgtgttgt acatacagag gtaactatca atatttaagt | 1174 |
| ttgttgctgt caagattttt tttgtaactt caaatataga gatattttg tacgttatat | 1234 |
| attgtattaa gggcatttta aaagcaatta tattgtcctc ccctatttta agacgtgaat | 1294 |
| gtctcagcga ggtgtaaagt tgttcgccgc gtggaatgtg agtgtgtttg tgtgcatgaa | 1354 |
| agagaaagac tgattacctc ctgtgtggaa gaaggaaaca ccgagtctct gtataatcta | 1414 |
| tttacataaa atgggtgata tgcgaacagc aaacc | 1449 |

<210> SEQ ID NO 2
<211> LENGTH: 185
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
| Met | Lys | Leu | Val | Ser | Val | Ala | Leu | Met | Tyr | Leu | Gly | Ser | Leu | Ala Phe |
| 1 | | | | 5 | | | | | 10 | | | | | 15 |

-continued

```
Leu Gly Ala Asp Thr Ala Arg Leu Asp Val Ala Ser Glu Phe Arg Lys
             20                  25                  30

Lys Trp Asn Lys Trp Ala Leu Ser Arg Gly Lys Arg Glu Leu Arg Met
         35                  40                  45

Ser Ser Ser Tyr Pro Thr Gly Leu Ala Asp Val Lys Ala Gly Pro Ala
     50                  55                  60

Gln Thr Leu Ile Arg Pro Gln Asp Met Lys Gly Ala Ser Arg Ser Pro
 65                  70                  75                  80

Glu Asp Ser Ser Pro Asp Ala Ala Arg Ile Arg Val Lys Arg Tyr Arg
                 85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 3
<211> LENGTH: 52
<212> TYPE: PRT
<213> ORGANISM: Homo sapiens
<220> FEATURE:
<221> NAME/KEY: mat_peptide
<222> LOCATION: (1)..(52)
<223> OTHER INFORMATION: Mature adrenomedullin, corresponding to
      positions 95-146 of preproadrenomedullin (SEQ ID NO: 2)

<400> SEQUENCE: 3

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
             20                  25                  30

Phe Thr Asp Lys Asp Lys Asp Asn Val Ala Pro Arg Ser Lys Ile Ser
         35                  40                  45

Pro Gln Gly Tyr
     50

<210> SEQ ID NO 4
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Active peptide AM(11-22), corresponding to
      positions 11-22 of adrenomedullin (SEQ ID NO: 3) and positions
      105-116 of preproadrenomedullin (SEQ ID NO: 2).

<400> SEQUENCE: 4

Leu Arg Ser Phe Gly Cys Arg Phe Gly Thr Cys Thr
 1               5                  10
```